US007655438B2

(12) United States Patent
Ferrandis

(10) Patent No.: US 7,655,438 B2
(45) Date of Patent: Feb. 2, 2010

(54) METHOD FOR PREPARING RECOMBINANT HETEROCARPINE

(75) Inventor: Eric Ferrandis, Saint Remy les Chevreuse (FR)

(73) Assignee: Societe de Conseils de Recherches et d'Application Scientifiques (S.C.R.A.S.), Paris (FR)

( * ) Notice: Subject to any disclaimer, the term of this patent is extended or adjusted under 35 U.S.C. 154(b) by 537 days.

(21) Appl. No.: 10/535,545

(22) PCT Filed: Dec. 9, 2003

(86) PCT No.: PCT/FR03/03629

§ 371 (c)(1), (2), (4) Date: May 18, 2005

(87) PCT Pub. No.: WO2004/063376

PCT Pub. Date: Jul. 29, 2004

(65) Prior Publication Data

US 2006/0228773 A1 Oct. 12, 2006

(30) Foreign Application Priority Data

Dec. 10, 2002 (FR) .................................. 02 15563

(51) Int. Cl.

| | |
|---|---|
| *C07H 21/04* | (2006.01) |
| *C07K 14/415* | (2006.01) |
| *C12N 15/29* | (2006.01) |
| *C12P 21/06* | (2006.01) |
| *A61K 38/16* | (2006.01) |
| *C07K 16/16* | (2006.01) |
| *G01N 33/53* | (2006.01) |

(52) U.S. Cl. ........................ 435/69.1; 514/12; 530/370; 536/23.6

(58) Field of Classification Search ................ 435/69.1; 514/12; 530/370; 536/23.6
See application file for complete search history.

(56) References Cited

U.S. PATENT DOCUMENTS 7,385,024 B2 * 6/2008 Ferrandis et al. ............ 530/300

FOREIGN PATENT DOCUMENTS

WO PCT/FR02/00691 9/2002

OTHER PUBLICATIONS

Hurteau et al. (Anal Biochem. 307:304-315 (2002)).*
Lin et al Biochemistry USA vol. 14:1559-1563 (1975).*
Vile et al (Gene Therapy, vol. 7, pp. 2-8, 2000.*
Rochlitz C. F. (Swiss Medicine Weekly, 131:4-9, 2001).*
Haupt (Exp. Biol. Med. 227:227-237 (2002)).*
Verma, Nature, vol. 389, pp. 239-242, 1997.*
Campbell, Biology, 3rd Ed, the Benjamin/Cummings Publishing Company, Inc., 1993 (p. 321).*
The Free Dictionary definition of "antisense" (pp. 1-3) (Dec. 22, 2008).*
Sambrook and Russell (Molec. Cloning, vol. 2; Protocol 1 (2001)) (pp. 8.18-8.22).*
Smith et al. (Nature Biotechnology 15:1222-1223 (1997)).*
Brenner (Trends in Genetics 15:132-133 (1999)).*

* cited by examiner

*Primary Examiner*—Lynn Bristol
(74) *Attorney, Agent, or Firm*—Hunton & Williams LLP

(57) ABSTRACT

A process for preparing recombinant heterocarpine with the complete sequence of heterocarpine (SEQ. ID. NO. 10), expression vectors comprising a polynucleotide encoding for heterocarpine, host cells transformed or transfected by said expression vectors as well as a process for obtaining heterocarpine by means of said transformed or transfected host cells are described where in the recombinant heterocarpine obtained is used to treat cancer.

23 Claims, No Drawings

METHOD FOR PREPARING RECOMBINANT HETEROCARPINE

This application is a national phase application of PCT/FR2003/003629, filed Dec. 9, 2003, which claims priority to FR 02/15563, filed Dec. 10, 2002.

A subject of the invention is a process for preparing recombinant heterocarpine.

Heterocarpine is a protein with anti-cancer properties described for the first time by the Applicant in Patent Application PCT WO 02/068461. This isolated protein has a molecular mass of approximately 90.9 kDa, comprises fragments of peptide sequences SEQ. ID. NO. 1, SEQ. ID. NO. 2 and SEQ. ID. NO. 3 (see the part of the description reserved for the sequence listing) and is capable of being obtained by extraction from *Pilocarpus heterophyllus* plant cells cultured in vitro as described in the abovementioned patent application. However, the complete sequence of this protein remained unknown up to now, to the extent that cloning had not been carried out.

The present application now describes polynucleotides which can serve as a primer for cloning heterocarpine, the DNA encoding for heterocarpine, the mRNA corresponding to heterocarpine, expression vectors containing said mRNA, host cells transformed or transfected with these vectors as well as a process for preparing recombinant heterocarpine.

A subject of the present invention is therefore firstly an isolated polynucleotide comprising the polynucleotide sequence SEQ. ID. NO. 8. Preferably, said isolated polynucleotide consists of the polynucleotide sequence SEQ. ID. NO. 8.

A subject of the present invention is also an anti-sense polynucleotide comprising the sequence complementary to that of said isolated polynucleotide comprising the polynucleotide sequence SEQ. ID. NO. 8. Preferably, said anti-sense polynucleotide consists of the sequence complementary to the polynucleotide sequence SEQ. ID. NO. 8.

The invention also relates to an isolated polynucleotide comprising the polynucleotide sequence SEQ. ID. NO. 8 or one of the fragments of the latter, said polynucleotide being such that it encodes a polypeptide having at least one immunological and/or biological activity characteristic of a protein binding human GHRH and being associated with the modulation of cell proliferation. Preferably, said isolated polynucleotide is such that it consists of the polynucleotide sequence SEQ. ID. NO. 8 or one of the fragments of the latter.

In particular, the invention therefore relates to the isolated polynucleotide of nucleotide sequence SEQ. ID. NO. 9 or the isolated polynucleotide of nucleotide sequence complementary to the nucleotide sequence SEQ. ID. NO. 9.

Heterocarpine, in other words the protein of sequence SEQ. ID. NO. 10, is encoded by the fragment of the polynucleotide of polynucleotide sequence SEQ. ID. NO. 8 contained between the bases at positions 115 (initiation codon ATG encoding for a methionine) and 2437 (stop codon UAA), i.e. by the polynucleotide sequence SEQ. ID. NO. 9.

The invention therefore also relates to an expression vector comprising an isolated polynucleotide comprising the polynucleotide sequence SEQ. ID. NO. 8 or one of the fragments of the latter or the sequence complementary to the polynucleotide sequence SEQ. ID. NO. 8 or one of the fragments of the latter, the polypeptide encoded by said isolated polynucleotide having at least one immunological and/or biological activity characteristic of a protein binding human GHRH and being associated with the modulation of cell proliferation. Preferably, said expression vector will comprise the polynucleotide sequence SEQ. ID. NO. 9 or the sequence complementary to the polynucleotide sequence SEQ. ID. NO. 9.

The invention similarly relates to a host cell transformed or transfected with said expression vector.

The invention also relates to an isolated polypeptide comprising a polypeptide of sequence SEQ. ID. NO. 14 or one of its fragments, said isolated polypeptide having at least one immunological and/or biological activity characteristic of a protein binding human GHRH and being associated with the modulation of cell proliferation. Preferably, said isolated polypeptide will consist of a polypeptide of sequence SEQ. ID. NO. 14 or one of its fragments. In particular, said polypeptide will have the sequence SEQ. ID. NO. 14.

A subject of the invention is also a monoclonal antibody, or an antigen-binding fragment of the latter, which specifically binds an isolated polypeptide as described previously, and in particular a monoclonal antibody, or an antigen-binding fragment of the latter, which specifically binds the protein of sequence SEQ. ID. NO. 14 but not the protein of sequence SEQ. ID. NO. 10.

The invention also relates to, as a medicament, an isolated polynucleotide comprising:
 the polynucleotide sequence SEQ. ID. NO. 8 or one of its fragments, or
 the polynucleotide sequence SEQ. ID. NO. 9 or one of its fragments, said isolated polynucleotide being such that it encodes an isolated polypeptide having at least one immunological and/or biological activity characteristic of a protein binding human GHRH and being associated with the modulation of cell proliferation.

Preferably, the isolated polynucleotide will consist of the polynucleotide of polynucleotide sequence SEQ. ID. NO. 8 or one of its fragments, or the polynucleotide of polynucleotide sequence SEQ. ID. NO. 9 or one of its fragments.

In particular, said isolated polynucleotide will consist of the polynucleotide of polynucleotide sequence SEQ. ID. NO. 8 or the polynucleotide of polynucleotide sequence SEQ. ID. NO. 9.

Moreover, said isolated polynucleotide used as a medicament is preferably present in a viral vector, said viral vector being for example selected from the group consisting of an adenovirus, an associated adenovirus, a retrovirus and a pox virus.

The invention also relates to, as a medicament, an isolated polypeptide comprising a polypeptide of sequence SEQ. ID. NO. 14 or one of its fragments, said isolated polypeptide having at least one immunological and/or biological activity characteristic of a protein binding human GHRH and being associated with the modulation of cell proliferation. Preferably, said isolated polypeptide will consist of a polypeptide of sequence SEQ. ID. NO. 14 or one of its fragments. In particular, said polypeptide will have the sequence SEQ. ID. NO. 14.

The invention also relates to, as a medicament, a monoclonal antibody, or an antigen-binding fragment of the latter, which specifically binds an isolated polypeptide comprising the protein encoded by the polynucleotide sequence SEQ. ID. NO. 9 or one of the fragments of the latter or by a sequence complementary to the polynucleotide sequence SEQ. ID. NO. 9 or one of the fragments of the latter, said isolated polypeptide having at least one immunological and/or biological activity characteristic of a protein binding human GHRH and being associated with the modulation of cell proliferation. Preferably, said monoclonal antibody or said fragment of the antigen of the latter specifically binds an isolated polypeptide consisting of the protein encoded by the polynucleotide sequence SEQ. ID. NO. 9 or one of the fragments of the latter or by a sequence complementary to the polynucleotide sequence SEQ. ID. NO. 9 or one of the fragments of the latter. Yet more preferentially, said monoclonal antibody or said fragment of the antigen of the latter specifically binds an isolated polypeptide consisting of the protein encoded by the polynucleotide sequence SEQ. ID. NO. 9 or by a sequence complementary to the polynucleotide sequence SEQ. ID. NO. 9 (in other words the protein of sequence SEQ. ID. NO. 10).

Another subject of the invention is a pharmaceutical composition comprising, as active ingredient, an isolated polynucleotide comprising:
 the polynucleotide sequence SEQ. ID. NO. 8 or one of its fragments, or
 the polynucleotide sequence SEQ. ID. NO. 9 or one of its fragments, said isolated polynucleotide being such that it encodes an isolated polypeptide having at least one immunological and/or biological activity characteristic of a protein binding human GHRH and being associated with the modulation of cell proliferation, with one or more pharmaceutically acceptable excipients.

Preferably, the isolated polynucleotide serving as active ingredient will consist of the polynucleotide of polynucleotide sequence SEQ. ID. NO. 8 or one of its fragments or the polynucleotide of polynucleotide sequence SEQ. ID. NO. 9 or one of its fragments.

In particular, the isolated polynucleotide serving as active ingredient will consist of the polynucleotide of polynucleotide sequence SEQ. ID. NO. 8 or the polynucleotide of polynucleotide sequence SEQ. ID. NO. 9.

Said isolated polynucleotide incorporated into a pharmaceutical composition according to the invention is preferably present in a viral vector, said viral vector being for example selected from the group consisting of an adenovirus, an associated adenovirus, a retrovirus and a pox virus.

The invention also relates to a pharmaceutical composition comprising an isolated polypeptide comprising a polypeptide of sequence SEQ. ID. NO. 14 or one of its fragments, said isolated polypeptide having at least one immunological and/or biological activity characteristic of a protein binding human GHRH and being associated with the modulation of cell proliferation. Preferably, said isolated polypeptide will consist of a polypeptide of sequence SEQ. ID. NO. 14 or one of its fragments. In particular, said polypeptide will have the sequence SEQ. ID. NO. 14.

A subject of the invention is moreover a pharmaceutical composition comprising a monoclonal antibody, or an antigen-binding fragment of the latter, which specifically binds an isolated polypeptide comprising at least one fragment of the protein encoded by the polynucleotide sequence SEQ. ID. NO. 9 or by a sequence complementary to the polynucleotide sequence SEQ. ID. NO. 9, said isolated polypeptide having at least one immunological and/or biological activity characteristic of a protein binding human GHRH and being associated with the modulation of cell proliferation, said composition comprising moreover one or more pharmaceutically acceptable excipients. Preferably, said pharmaceutical composition according to the invention is such that it comprises a monoclonal antibody, or an antigen-binding fragment of the latter, which specifically binds an isolated polypeptide consisting of the protein encoded by the polynucleotide sequence SEQ. ID. NO. 9 or one of the fragments of the latter or by a sequence complementary to the polynucleotide sequence SEQ. ID. NO. 9 or one of the fragments of the latter.

In particular, the invention relates to a pharmaceutical composition comprising a monoclonal antibody, or an antigen-binding fragment of the latter, which specifically binds the protein encoded by the polynucleotide sequence SEQ. ID. NO. 9 or by the sequence complementary to the polynucleotide sequence SEQ. ID. NO. 9 (in other words the protein of sequence SEQ. ID. NO. 10) with one or more pharmaceutically acceptable excipients.

Another subject of the invention is the use of an isolated polynucleotide comprising:
 the polynucleotide sequence SEQ. ID. NO. 8 or one of its fragments, or
 the polynucleotide sequence SEQ. ID. NO. 9 or one of its fragments, said isolated polynucleotide being such that it encodes an isolated polypeptide having at least one immunological and/or biological activity characteristic of a protein binding human GHRH and being associated with the modulation of cell proliferation, for preparing a medicament intended to treat a proliferative disease.

Preferably, the isolated polynucleotide used will consist of the polynucleotide of polynucleotide sequence SEQ. ID. NO. 8 or one of its fragments or the polynucleotide of polynucleotide sequence SEQ. ID. NO. 9 or one of its fragments.

In particular, the isolated polynucleotide used will consist of the polynucleotide of polynucleotide sequence SEQ. ID. NO. 8 or the polynucleotide of polynucleotide sequence SEQ. ID. NO. 9.

Said isolated polynucleotide used is preferably present in a viral vector, said viral vector being for example selected from the group consisting of an adenovirus, an associated adenovirus, a retrovirus and a pox virus.

The present invention also relates to the use of an isolated polypeptide comprising a polypeptide of sequence SEQ. ID. NO. 14 or one of its fragments, said isolated polypeptide having at least one immunological and/or biological activity characteristic of a protein binding human GHRH and being associated with the modulation of cell proliferation, for preparing a medicament intended to treat a proliferative disease. Preferably, said isolated polypeptide will consist of a polypeptide of sequence SEQ. ID. NO. 14 or one of its fragments. In particular, said polypeptide will have the sequence SEQ. ID. NO. 14.

Alternatively, still according to the present invention, a monoclonal antibody, or an antigen-binding fragment of the latter, which specifically binds an isolated polypeptide comprising the protein encoded by the polynucleotide sequence SEQ. ID. NO. 9 or one of the fragments of the latter or by a sequence complementary to the polynucleotide sequence SEQ. ID. NO. 9 or one of the fragments of the latter, said isolated polypeptide having at least one immunological and/or biological activity characteristic of a protein binding human GHRH and being associated with the modulation of cell proliferation, can be used for preparing a medicament intended to treat a proliferative disease. Preferably, said monoclonal antibody or said fragment of the antigen of the latter will specifically bind a polypeptide consisting of the protein encoded by the polynucleotide sequence SEQ. ID. NO. 9 or one of the fragments of the latter or by a sequence complementary to the polynucleotide sequence SEQ. ID. NO. 9 or one of the fragments of the latter.

In particular, a monoclonal antibody, or an antigen-binding fragment of the latter, which specifically binds an isolated polypeptide encoded by the polynucleotide sequence SEQ. ID. NO. 9 or by the sequence complementary to the polynucleotide sequence SEQ. ID. NO. 9 (in other words, a monoclonal antibody, or an antigen-binding fragment of the latter, which specifically binds the protein of sequence SEQ. ID. NO. 10), can be used for preparing a medicament intended to treat a proliferative disease.

According to preferred variants of the abovementioned uses, the proliferative disease to be treated by the polypeptide or the polynucleotide described previously is a cancer. According to yet more preferred variants, the cancer is chosen from the group consisting of prostate cancer, breast cancer, lung cancer (and in particular small-cell lung cancer) and colorectal cancer. Breast cancer and small-cell lung cancer are yet more particularly preferred.

The invention moreover offers a method for preparing an isolated polypeptide comprising the protein encoded by the polynucleotide sequence SEQ. ID. NO. 9 or SEQ. ID. NO. 13 or one of the fragments of the latter or by a sequence complementary to the polynucleotide sequence SEQ. ID. NO. 9 or one of the fragments of the latter, said isolated polypeptide having at least one immunological and/or biological activity characteristic of a protein binding human GHRH and being associated with the modulation of cell proliferation, said preparation method comprising the following successive stages:

(a) culture, under suitable conditions in order to obtain the expression of said polypeptide of a host cell transformed or transfected with an expression vector comprising an isolated polynucleotide comprising the polynucleotide sequence SEQ. ID. NO. 9 or SEQ. ID. NO. 13, the sequence complementary to the polynucleotide sequence SEQ. ID. NO. 9 or SEQ. ID. NO. 13 or also one of the fragments of the latter, said isolated polypeptide having at least one immunological and/or biological activity characteristic of a protein binding human GHRH and being associated with the modulation of cell proliferation, and (b) isolation of the polypeptide from the host cell cultures.

Preferably, said preparation method will relate to the preparation of an isolated polypeptide consisting of the protein encoded by the polynucleotide sequence SEQ. ID. NO. 9 or one of the fragments of the latter or by a sequence complementary to the polynucleotide sequence SEQ. ID. NO. 9 or one of the fragments of the latter, said isolated polypeptide having at least one immunological and/or biological activity characteristic of a protein binding human GHRH and being associated with the modulation of cell proliferation, said preparation method comprising the following successive stages:

(a) culture, under suitable conditions in order to obtain the expression of said polypeptide of a host cell transformed or transfected with an expression vector comprising an isolated polynucleotide comprising the polynucleotide sequence SEQ. ID. NO. 9 or SEQ. ID. NO. 13, the sequence complementary to the polynucleotide sequence SEQ. ID. NO. 9 or SEQ. ID. NO. 13 or also one of the fragments of the latter, said isolated polypeptide having at least one immunological and/or biological activity characteristic of a protein binding human GHRH and being associated with the modulation of cell proliferation, and (b) isolation of the polypeptide from the host cell cultures.

In particular, the object of said method will be the preparation of the isolated polypeptide encoded by the polynucleotide sequence SEQ. ID. NO. 9 or SEQ. ID. NO. 13 or by the sequence complementary to the polynucleotide sequence SEQ. ID. NO. 9 or SEQ. ID. NO. 13 (in other words, the preparation of the protein of sequence SEQ. ID. NO. 10).

According to a yet more preferred variant of said method, the latter will relate to the preparation of the protein of sequence SEQ. ID. NO. 10 and will comprise the following stages:

(a) culture, under suitable conditions in order to obtain the expression of said polypeptide of a host cell transformed or transfected with an expression vector comprising an isolated polynucleotide comprising the polynucleotide sequence SEQ. ID. NO. 9 or SEQ. ID. NO. 13 or the sequence complementary to the polynucleotide sequence SEQ. ID. NO. 9 or SEQ. ID. NO. 13, said isolated polypeptide having at least one immunological and/or biological activity characteristic of a protein binding human GHRH and being associated with the modulation of cell proliferation, and (b) isolation of the polypeptide from the host cell cultures.

The present invention also offers a process for identifying compounds capable of binding human GHRH and modulating cell proliferation, which comprises the following successive stages:

(a) bringing each candidate compound into contact with an isolated polypeptide comprising:

either a fragment of the protein encoded by the polynucleotide sequence SEQ. ID. NO. 9 or by a sequence complementary to the polynucleotide sequence SEQ. ID. NO. 9, or a fragment of the protein encoded by the polynucleotide sequence SEQ. ID. NO. 13 or by a sequence complementary to the polynucleotide sequence SEQ. ID. NO. 13, under conditions and for a time sufficient to allow the candidate agent to bind to the polypeptide, said isolated polypeptide having at least one immunological and/or biological activity characteristic of a protein binding human GHRH and being associated with the modulation of cell proliferation, and (b) detection of the binding of each candidate compound to said polypeptide and identification, from the candidate compounds, of the compounds capable of binding human GHRH and modulating cell proliferation.

In particular, said method for the identification of compounds capable of binding human GHRH and modulating cell proliferation will comprise, in its stage (a), bringing each candidate compound, under conditions and for a time sufficient to allow the candidate agent to bind to the polypeptide, into contact with the isolated polypeptide encoded by the polynucleotide sequence SEQ. ID. NO. 9 or by the sequence complementary to the polynucleotide sequence SEQ. ID. NO. 9 (in other words, with the protein of sequence SEQ. ID. NO. 10).

An alternative method for the identification of compounds capable of binding human GHRH and modulating cell proliferation comprises the following successive stages:

(a) bringing each candidate compound, under conditions and for a time sufficient to allow the candidate agent and the cell to interact, into contact with a cell capable of expressing an isolated polypeptide comprising:

either a fragment of the protein encoded by the polynucleotide sequence SEQ. ID. NO. 9 or by a sequence complementary to the polynucleotide sequence SEQ. ID. NO. 9, or a fragment of the protein encoded by the polynucleotide sequence SEQ. ID. NO. 13 or by a sequence complementary to the polynucleotide sequence SEQ. ID. NO. 13, said isolated polypeptide having at least one immunological and/or biological activity characteristic of a protein binding human GHRH and modulating cell proliferation, and (b) determination of the effect of each candidate compound on the cell concentration of polypeptide and identification, from the candidate compounds, of the compounds capable of binding human GHRH and modulating cell proliferation.

In particular, said alternative method will comprise, in its stage (a), bringing each candidate compound, under conditions and for a time sufficient to allow the candidate agent and the cell to interact, into contact with a cell capable of expressing the isolated polypeptide encoded by the polynucleotide sequence SEQ. ID. NO. 9 or by the sequence complementary to the polynucleotide sequence SEQ. ID. NO. 9 (in other words, a cell capable of expressing the protein of sequence SEQ. ID. NO. 10).

According to preferred methods of implementing the processes for identifying compounds capable of binding human GHRH and modulating cell proliferation described above, the candidate compounds will originate from small molecule libraries resulting from combinatorial chemistry programmes.

The pharmacological properties obtained for the polynucleotides and polypeptides according to the invention make the latter suitable for pharmaceutical use. In fact, the isolated polypeptides comprising:

either a fragment of the protein encoded by the polynucleotide sequence SEQ. ID. NO. 9 or by a sequence complementary to the polynucleotide sequence SEQ. ID. NO. 9, or a fragment of the protein encoded by the polynucleotide sequence SEQ. ID. NO. 13 or by a sequence complementary to the polynucleotide sequence SEQ. ID. NO. 13, which have at least one immunological and/or biological activity characteristic of a protein binding human GHRH and being associated with the modulation of cell proliferation, as well as the polynucleotides encoding for said polypeptides, can, according to the invention, be administered to cancer patients in order to slow down the progression of their tumors or to make said tumors regress.

In the above methods, the protein binding human GHRH and being associated with the modulation of cell proliferation can in particular be the isolated polypeptide encoded by the polynucleotide sequence SEQ. ID. NO. 9 or by the sequence complementary to the polynucleotide sequence SEQ. ID. NO. 9 (in other words, the protein of sequence SEQ. ID. NO. 10).

Finally, the invention relates to the polynucleotides of sequence SEQ. ID. NO. 4, SEQ. ID. NO. 5, SEQ. ID. NO. 11 and SEQ. ID. NO. 12, which can in particular be used as primer in the PCR reactions of heterocarpine cloning.

The different elements mentioned above will become evident to a person skilled in the art having once read the more detailed description of the different features of the invention.

DETAILED DESCRIPTION OF THE DIFFERENT FEATURES OF THE INVENTION

As mentioned above, the present invention is generally directed towards products and methods intended to modulate cell growth and to treat cancer. The present invention is based, in part, on the identification of "sequences associated with the modulation of cell proliferation" which are polypeptide and polynucleotide sequences associated with the modulation of cell proliferation. Such cDNA molecules can be prepared from preparations of RNA or mRNA using standard techniques, such as reverse transcription. Similarly, a protein or a polypeptide associated with differentiation comprises the sequence encoded by an mRNA associated with cell differentiation.

The pharmaceutical compositions described here can include one or more polypeptides, nucleic acid sequences and/or antibodies. The polypeptides of the present invention include at least one portion of the protein or a variant of the latter binding human GHRH and being associated with the modulation of cell proliferation. The nucleic acid sequences of the present invention include a DNA or RNA sequence which encodes at least for a portion of such a polypeptide or which is complementary to such an encoding sequence.

The antibodies are proteins of the immune system or fragments binding to the antigen of the latter, which are capable of binding a portion of the polypeptides described above.

Polynucleotides, Polypeptides and Proteins According to the Invention:

A particular subject of the present invention is the polynucleotides of sequence SEQ. ID. NO. 8, SEQ. ID. NO. 9 or SEQ. ID. NO. 13 as well as the polypeptide or the protein of sequence SEQ. ID. NO. 14.

The invention also comprises the polynucleotides having polynucleotide sequences at least 75%, preferably at least 85% and yet more preferentially at least 90% or even 95%, homologous to the sequences of the polynucleotides described above, in particular to the sequences SEQ. ID. NO. 8, SEQ. ID. NO. 9 and SEQ. ID. NO. 13. This also applies mutatis mutandis to the other polynucleotides, polypeptides and proteins forming part of the invention, and in particular to the protein of sequence SEQ. ID. NO. 14.

The degree of homology expressed in % is calculated as follows:

$$100-100\times(N'/N)$$

with N' representing the number of nucleotides or amino acids modified with respect to the sequence SEQ. ID. NO. 8, SEQ. ID. NO. 9, SEQ. ID. NO. 10, SEQ. ID. NO. 13 or SEQ. ID. NO. 14 and N the number of nucleotides of the sequence SEQ. ID. NO. 8, SEQ. ID. NO. 9, SEQ. ID. NO. 10, SEQ. ID. NO. 13 or SEQ. ID. NO. 14.

According to the invention, the polynucleotide sequences which encode the polypeptides or proteins of the invention, and fragments or fusion proteins of these polypeptides or proteins, can be used in order to generate recombinant DNA molecules which direct the expression of these polypeptides or proteins, or an active portion of the latter, in appropriate host cells. Alternatively, polynucleotide sequences which hybridize with portions of the polynucleotide sequences according to the invention can also be used in nucleic acid hybridization, Southern blot, Northern blot tests, etc.

Because of the degeneration of the genetic encode, other DNA sequences substantially encoding for the amino acid sequence of the polypeptides or proteins of the invention can be used for the cloning and expression of said polypeptides or proteins. Such DNA sequences include those capable of hybridizing the polynucleotide sequences of the polynucleotides of the invention under certain stringency conditions which can be adjusted in several ways. For example, during polymerase chain reaction (PCR), the temperature at which the primers hybridize to the matrix or the concentrations of MgCl$_2$ in the reaction buffer, can be adjusted. During the use of radiolabelled DNA fragments, or oligonucleotides to probe membranes, the stringency can be adjusted by changing the ionic strengths of the washing solutions or by carefully controlling the washing temperature.

Preferentially, such a homologous nucleotide sequence hybridizes specifically with the sequence complementary to the sequence SEQ. ID. NO. 8, SEQ. ID. NO. 9 or SEQ. ID. NO. 13 under stringent conditions (or conditions of "high" stringency). The parameters defining the conditions of stringency depend on the temperature at which 50% of the paired strands separate ($T_m$).

For the sequences comprising more than 30 bases, and according to Sambrook et al. (*Molecular cloning: A Laboratory Manual*, Cold Spring Harbor Laboratories, Cold Spring Harbor, N.Y., 1989), $T_m$ is defined by the equation:

$$T_m = 81.5 + 0.41 \times (\% \ G + C) + 16.6 \times \log [\text{cations}] - 0.63 \times (\% \ \text{formamide}) - (600/\text{number of bases})$$

For the present invention, the stringency conditions of are called "high" when a hybridization temperature 10° C. below $T_m$ and hybridization buffers containing a 6×SSC (0.9 M sodium chloride and 0.09 M sodium citrate) solution are used. Under such conditions, the polynucleotides of aspecific sequences will not hybridize with the polynucleotide of the sequence complementary to the sequence SEQ. ID. NO. 8, SEQ. ID. NO. 9 or SEQ. ID. NO. 13.

Altered DNA sequences which can be used in accordance with the present invention include deletions, additions or substitutions of different nucleotide residues resulting in a sequence which encodes the same gene product or equivalent function. The gene product can also contain deletions, additions or substitutions of amino acid residues in the sequences of the proteins of the invention, which result in so-called silent changes, thus producing polypeptides and proteins of equivalent function.

Such amino acid substitutions can be carried out on the basis of the polarity, charge, solubility, hydrophobicity, hydrophilicity, and/or amphipatic nature of the residues involved.

For example, negatively-charged amino acids include aspartic acid and glutamic acid, positively-charged amino acids include lysine and arginine, amino acids with polar groups having close hydrophobicity values include leucine, isoleucine, valine; glycine, alanine; asparagine, glutamine; serine, threonine; phenylalanine, tyrosine.

The DNA sequences of the present invention can be modified in order to alter the polynucleotide sequences according to the invention for numerous reasons including in a non-limitative manner alterations which modify the process and the expression of the gene product. For example, mutations can be introduced using techniques well known to a person skilled in the art, for example directed mutagenesis, the insertion of new restriction sites, the alteration of the glycosylations, phosphorylation, etc.

In particular, in certain expression systems such as yeast, the host cell can over-glycosylate the gene product. In such a system, it is preferable to alter the polynucleotide sequences in order to eliminate the glycosylation sites. Within the scope of the disclosure of the present invention modified polynucleotide sequences also figure, linked with heterologous sequences in order to encode a fusion protein. The fusion protein (which can be for example the protein of sequence SEQ. ID. NO. 14) can be modified in order to contain a cleavage site located between the sequence of the protein according to the invention (for example the sequence SEQ. ID. NO. 10) and the sequence of the heterologous protein, such that the sequence of the protein according to the invention can be cleaved from the heterologous part.

Polynucleotides Encoding for Polypeptides Associated with the Modulation of Cell Proliferation:

Any polynucleotide which encodes a polypeptide or a portion or a variant of the latter as described here, binding human GHRH and being associated with the modulation of cell proliferation, is covered by the present invention. Such polynucleotides can be single-strand (encoding or anti-sense) or double-strand and can be DNA (genomic, cDNA or synthetic) or RNA molecules.

The polynucleotides encoding for polypeptides binding human GHRH and being associated with the modulation of cell proliferation can be prepared using any technique available to a person skilled in the art. For example, such a polynucleotide can be amplified via a polymerase chain reaction (PCR) from cDNA prepared from cells. For this approach, specific primers can be designed and ordered or synthesized; these primers are based on the sequence of said polynucleotide. An amplified portion can then be used in order to isolate the complete gene of any cell or any tissue from a genomic DNA library or from a cDNA library, by means of techniques well known to a person skilled in the art and briefly recalled below. Alternatively, a complete gene can be constructed from several PCR fragments. The cDNA molecules encoding for a protein binding human GHRH and being associated with the modulation of cell proliferation, or a portion of the latter, can also be prepared by screening a cDNA library obtained for example from mRNA of cells or tissues. Such libraries can be commercially available or can be prepared using the standard techniques (cf. Sambrook et al., *Molecular cloning: A Laboratory Manual*, Cold Spring Harbor Laboratories, Cold Spring Harbor, N.Y., 1989).

Alternatively, other screening techniques well known to a person skilled in the art can be used.

A cDNA molecule encoding for a polypeptide binding human GHRH and being associated with the modulation of cell proliferation can be sequenced by using the standard techniques using enzymes such as the Klenow fragment of DNA polymerase I, Sequenase X (US Biochemical Corp., Cleveland, Ohio, United States), Taq polymerase (Perkin Elmer, Foster City, Calif., United States), thermostable polymerase T7 (Amersham, Chicago, Ill., United States) or a combination of recombinant polymerases and exonucleases with a rereading activity such as the Elongase amplification system (Gibco BRL, Gaithersburg, Md., United States). An automatic sequencing system can be used, using instruments available from commercial suppliers such as Perkin Elmer and Pharmacia.

The partial sequence of a cDNA can be used in order to identify a polynucleotide sequence which encodes the complete protein associated with the modulation of cell proliferation using standard techniques well known to a person skilled in the art. Among these techniques, a cDNA library is screened using one or more polynucleotide probes using RecA recombination properties (ClonCapture cDNA Selection Kit, Clontech Laboratories, United States).

For the hybridization techniques, a partial sequence can be radiolabelled (for example by nick translation or labelling of the ends using $^{32}$P or $^{33}$P) using standard techniques. A bacteria or bacteriophage library is then screened by hybridization on filters containing denatured bacterial colonies (or blots containing phage plates) with the labelled probe (cf. Sambrook et al., *Molecular cloning: A Laboratory Manual*, Cold Spring Harbor Laboratories, Cold Spring Harbor, N.Y., 1989). The positive colonies or plates are then selected and amplified and the DNA is isolated for future analyses.

The complete sequence can then be determined using standard techniques. The overlapping sequences are then assembled into a continuous single sequence. A complete cDNA molecule can be generated by ligation of the fragments of interest using standard techniques.

Alternatively, numerous techniques based on amplification exist for obtaining a complete encoding sequence from a partial cDNA sequence. Among these, the amplification is generally carried out via PCR. All of the kits commercially available can be used for the amplification stages. The primers can be designed using, for example, software well known in the art. The nucleotide primers are preferably molecules with 20 to 30 nucleotides having a guanine and cytosine content of at least 50% and which hybridize with the target sequence at temperatures comprised between 50 and 72° C. The amplified region can be sequenced as described above and the overlapping sequences assembled into a continuous sequence.

Among the alternative approaches, sequences adjacent to the partial sequence can be found by amplification with a primer of the binding sequence and a primer specific to a known region. The amplified sequences are then subjected to a second amplification cycle.

Additional techniques include capture PCR (Lagerstrom et al., *PCR Methods Applic*. (1991), 1, 111-19) and progressive PCR (Parker et al., *Nucl. Acids. Res*. (1991), 19, 3055-60). Other methods using amplification can also be used in order to obtain a complete cDNA sequence.

It is possible to obtain a complete cDNA sequence by analyzing the sequences deposited in the public "Expressed Sequence Tags" (ESTs) bases available from GenBank. Research covering the ESTs can be carried out using computer programmes well known to a person skilled in the art (for example NCBI BLAST) and such ESTs can be used to generate a continuous complete sequence.

Variants of the polynucleotide sequences described above (in particular sequences SEQ. ID. NO. 8, SEQ. ID. NO. 9 and SEQ. ID. NO. 13) are also included within the scope of the present invention. The polynucleotide variants can contain one or more substitutions, deletions or insertions (cf. also above in the part entitled "Polynucleotides, polypeptides and proteins according to the invention").

A portion of the sequence complementary to the encoding sequence (i.e. an anti-sense polynucleotide) can also be used as a probe or modulator of gene expression. The cDNA construct which can be transcribed to anti-sense RNA can be introduced into cells or tissues in order to facilitate the production of anti-sense RNA. An anti-sense polynucleotide can be used, as described here, in order to inhibit the expression of a gene associated with the modulation of cell proliferation. The anti-sense technology can be used in order to control gene expression by forming a triple-helix, which compromises the ability of the double helix to open sufficiently for the fixing of polymerases, transcription factors or regulation molecules (cf. Gee et al. in Huber and Carr, *Molecular and Immunologic Approaches* (1994), Futura Publishing Co., Mt. Kisco, N.Y.). Alternatively, an anti-sense molecule can be used to hybridize with a gene control region (for example a promoter or initiation site of the transcription) and to block the transcription of the gene, or to block the translation by inhibiting the fixing of ribosomes to the transcript.

The polynucleotides can then be modified in order to increase their stability in vivo. Possible modifications include (but are not limited to): the addition of sequences to the 5' and/or 3' ends; the use of phosphorothioate or 2' O-methyl rather than phosphodiesterase bonds in the backbone; and/or the introduction of bases such as inosine, queosine and wybutosine as well as acetyladenine, methylthioadenine and modified forms of adenine, cytidine, guanine, thymine and uridine.

Other variations of the polynucleotides of the present invention have moreover already been described previously in the part entitled "Polynucleotides, polypeptides and proteins according to the invention".

The nucleotide sequences as described in the present invention can be joined to other nucleotide sequences using established recombinant DNA techniques. For example, a polynucleotide can be cloned in a large panel of expression vectors, including plasmids, phagemids, lambda phage derivatives and cosmids. The vectors of particular interest include the expression vectors, replication vectors and sequencing vectors. In general, a vector contains a functional replication origin in at least one organism, suitable endonuclease restriction sites and one or more selection markers. The presence of other elements will depend on the specific use desired by a person skilled in the art who will select the characteristics of the expression vector as a function of his requirements and the techniques available.

The polynucleotides can be formulated in order to enter the cell and express the corresponding polypeptide. Such formulations are particularly useful in therapy as described hereafter.

Persons skilled in the art will appreciate that several means exist for expressing a polynucleotide in a target cell, and that any appropriate technique can be used. For example, a polynucleotide can be incorporated into a viral vector such as an adenovirus or a retrovirus (but also into others). Techniques for incorporating DNA into such vectors are well known to a person skilled in the art. A retroviral vector can transfer or incorporate a gene for a selection marker and/or a screening entity such as a gene encoding for the ligand of a specific receptor of a target cell, in order to render the vector target-specific.

Other formulations for the polynucleotides include colloidal dispersion systems such as macromolecular complexes, nano-capsules, microspheres, spheres, and systems based on the use of lipids including oil/water emulsions, micelles, mixed micelles and liposomes. The preferred colloidal system for use for delivering the product in vitro and in vivo is the liposome (i.e. an artificial membrane vesicle).

Polypeptides Binding Human GHRH and Modulating Cell Proliferation:

Within the scope of the disclosure, the polypeptides of the present invention include at least one portion of the protein associated with the modulation of cell proliferation or a variant of the latter, said portion being immunologically and/or biologically active. Such polypeptides can have any length, including the complete protein, an oligopeptide (i.e. consisting of a relatively limited number of amino acids, such as 8-10 residues, joined by peptide bonds) or a peptide of intermediate size. A polypeptide can also comprise additional sequences.

Similarly, a polypeptide is "biologically active" if it has one or more structural, regulatory and/or biochemical functions starting with the native protein associated with the binding of human GHRH and being associated with the modulation of cell proliferation.

The presence of a biological activity can be determined according to processes well known to a person skilled in the art. However, by definition within the framework of the present invention, a polypeptide is considered as "having at least one immunological and/or biological activity characteristic of a protein binding human GHRH and being associated with the modulation of cell proliferation" once its inhibitory concentration $IC_{50}$ measured under the conditions described in Example 6 of the present Application is less than or equal to 10 nM (and preferably less than or equal to 1 nM).

For example, comparative studies of sequences can indicate a particular biological activity of the protein. Tests for evaluating said activity can then implemented on the basis of tests already known in the art. Certain portions and other variants of such proteins should also show this property according to an in vitro or in vivo test.

As already mentioned, the polypeptides according to the present invention can comprise one or more portions of a variant of the endogenous protein where the portion is immunologically and/or biologically active (i.e. the portion has one or more antigenic, immunogenic and/or biological characteristics of the complete protein). Preferably, such a portion is at least as active as the total protein during tests allowing the detection of such properties. A "variant" polypeptide is a polypeptide which differs from the native protein by substitutions, insertions, deletions and/or modifications of amino acids. Certain variants contain conservative substitutions. "A conservative substitution" is a substitution in which one amino acid is substituted by another amino acid having the same properties, such as those determined by a person skilled in the art who expects no change in the secondary structure, as well as in the hydropathic nature of the polypeptide. The amino acid substitutions can generally be carried out on the basis of similarity of polarity, charge, solubility, hydrophobicity, hydrophilicity, and/or amphipathic nature of the residues. For example, negatively-charged amino acids include aspartic acid and glutamic acid; positively-charged amino acids include lysine and arginine; and polar non-charged amino acids having similar hydrophobicity values include leucine, isoleucine and valine; glycine and alanine; asparagine and glutamine; serine, threonine, phenylalanine and tyrosine. Other amino acid groups which can represent conservative changes are in particular the following: (1) Ala, Pro, Gly, Glu, Asp, Gln, Asn, Ser, Thr; (2) Cys, Ser, Tyr, Thr (3) Val, Ile, Leu, Met, Ala, Phe; (4) Lys, Arg, His; and (5) Phe, Tyr, Trp, His. A variant can also, or alternatively, contain non-conservative changes.

Variants forming part of this invention also include polypeptides in which the primary structure of the native protein is modified by formation of covalent conjugates or not modified with other polypeptides or chemical structures such as lipid groups or glycosyl, or phosphate acetyl groups.

The present invention also includes polypeptides with or without glycosylation patterns. The polypeptides expressed in expression systems of yeast or mammal cells can, in terms of molecular weight and glycosylation pattern, be similar to or slightly different from the native molecule according to the expression system used.

The expression of DNA in bacteria such as E. Coli leads to non-glycosylated molecules. The N-glycosylation sites of the eucaryotic proteins are characterized by the triplet of amino acids Asn-A1-Z where A1 is any amino acid except Pro, and Z is a serine or a threonine.

Other variations of the polypeptides and proteins of the present invention have moreover already been described previously in the part entitled "Polypeptides and polynucleotides according to the invention".

In order to prepare a polypeptide variant, standard mutagenesis techniques, such as directed mutagenesis using a directed oligonucleotide, can be used.

In general, any expression vector known to a person skilled in the art can be used in order to express recombinant polypeptides of this invention. The expression can be obtained in any appropriate host cell which has been transformed or transfected with an expression vector containing a DNA sequence which encodes the recombinant polypeptide. Suitable host cells include procaryotic, higher eucaryotic or yeast cells. Preferably, the host cells used are E. Coli, yeast cells or mammal cells such as COS, CHO, HEK-293, MCF7 (human tumor cells isolated from a mammary carcinoma) or DU 145 (human tumor cells isolated from a prostate cancer).

Certain portions and other variants can also be generated by synthetic means using techniques well known to a person skilled in the art. For example, portions and other variants having less than 500 amino acids, preferably less than 100 amino acids and more preferentially less than 50 amino acids can be synthesized by chemical route. The polypeptides can be synthesized using solid phase synthesis techniques available commercially, such as the Merrifield resin synthesis method where the amino acids are sequentially added to a chain of amino acids during the synthesis process (cf. Merrifield, *J. Am. Chem. Soc.* (1963), 85, 2149-2146). Numerous other solid phase synthesis techniques are also available (for example the process of Roberge et al., *Science* (1995), 269, 202-204). Equipment for the automatic synthesis of polypeptides is commercially available from suppliers such as Applied Biosystems, Inc. (Foster City, Calif., United States); the synthesis of the polypeptides can then be carried out by following the manufacturer's recommendations.

Isolated Polynucleotides or Polypeptides:

In general, the polypeptides and polynucleotides described in the present invention are isolated. An "isolated" polypeptide or polynucleotide is a polynucleotide or a peptide removed from its original environment. For example, a natural protein is isolated if it is separated from the biological material with which it coexists in the natural system. A polynucleotide is considered as isolated if, for example, it is cloned in a vector which does not form part of the natural environment.

Antibodies and Fragments of the Latter:

The present invention provides binding agents, such as the antibodies which specifically bind the protein associated with the binding of human GHRH and being associated with the modulation of cell proliferation. Such an agent is referred to as "specifically binding" to the cell proliferation modulation protein if it reacts at a level which is detectable (for example by an ELISA test) with a protein associated with the modulation of cell proliferation or a portion or a variant of the latter and does not react in detectable manner with other proteins. "The binding" refers to a non-covalent association between 2 separate molecules such that a complex is formed. The binding ability can be evaluated, for example, by determination of the binding constant for the formation of the complex. The binding constant is the value obtained when the value of the concentration of the complex is divided by the product of the values of the concentration of the components. In general, 2 products are called "bound" when the binding constant reaches 103 l/mol. The binding constant can be determined using methods well known to a person skilled in the art.

Any agent capable of fulfilling the above criteria can be considered as a binding agent.

In the present invention, a binding agent is preferably an antibody or a fragment of the latter. The antibodies can be prepared by any technique available to a person skilled in the art (cf. Harlow and Lane, *Antibodies. A Laboratory Manual*, Cold Spring Harbor Laboratory, 1988). In general, the antibodies can be produced by cell culture techniques including the generation of monoclonal antibodies or via transfections of genes of antibodies in host cells of bacteria or mammals in order to produce recombinant antibodies.

Among other techniques, it is preferable to use those described hereafter. An immunogen containing the polypeptide is injected into a group of mammals (for example mice, rats, rabbits, sheep or goats). In this stage, the polypeptides of the present invention can serve as immunogens without modification. Alternatively, and particularly for small peptides, a better immune response can be induced if the polypeptide is joined to a transport protein such as bovine serum albumin or keyhole-limpet hemocyanin. The immunogen is injected into the host animal, preferably according to a predetermined schema, and the animals are bled periodically. Polyclonal antibodies specific to the polypeptide can thus be purified from such antisera, for example by affinity chromatography using the peptide coupled to an appropriate solid support.

In order to prepare an antibody specifically binding a protein of sequence A but not a protein of sequence B, the protein of sequence A is injected into the host animal, preferably according to a predetermined schema, and the animal are bled periodically. Polyclonal antibodies specific to the polypeptide of sequence A can thus be purified from such antisera, for example by affinity chromatography using the protein of sequence B coupled to an appropriate solid support. The corresponding eluate contains the antibody specifically binding a protein of sequence A but not a protein of sequence B.

Fusion Proteins:

Any fusion gene can be produced by a person skilled in the art in order to analyze the sub-cellular location of a protein according to the invention, in particular the sub-cellular location of the protein of sequence SEQ. ID. NO. 10. Numerous plasmidic constructions are available commercially such as Glutathione S Transferase (GST) protein or fluorescent proteins such as Green Fluorescent Protein (GFP) or also and non-exhaustively a polyhistidine tag.

Human eucaryotic host cells (for example HEK-293) are sub-cultured for 24 hours before the transfection protocol allowing normal metabolism of the cells and better transfection effectiveness. Increasing concentrations (1, 5 and 10 µg) of vector alone containing the developer protein (GFP, GST or Tag Histidine) or of vector containing the polynucleotide of sequence SEQ. ID. NO. 8 or the polynucleotide of sequence SEQ. ID. NO. 9 fused with the developer protein were produced using the reagent Effectene® according to the manufacturer's (Qiagen) recommendations.

The cells are then analyzed by confocal microscopy, for example, in order to detect the location of the protein. If the protein is suspected of being secreted for example, the supernatants are recovered, lyophilized, deposited on acrylamide gel and analyzed by the Western blot technique using antibodies directed against the developer protein.

Pharmaceutical Compositions:

According to certain features of the invention, products such as polypeptides, antibodies and/or nucleic acids can be incorporated into pharmaceutical compositions or vaccines. The pharmaceutical compositions comprise one or more of these products and one or more pharmaceutically acceptable excipients (carriers). Certain pharmaceutical compositions optionally usable as vaccines can comprise one or more polypeptides and an immune response activator, such as an adjuvant or liposome (into which the product is incorporated). The pharmaceutical compositions and the vaccines can moreover contain an administration system, such as biodegradable microspheres (and for example microspheres composed of lactic acid and glycolic acid copolymers or PLGA). The pharmaceutical compositions and the vaccines within the scope of the disclosure of the present invention can also contain other products being able to be biologically active or inactive.

A pharmaceutical composition or a vaccine can contain DNA encoding for one or more polypeptides as described above, such that the polypeptide is generated in situ. As mentioned previously, the DNA can be present in any administration form known to a person skilled in the art, including bacterial or viral expression systems of nucleic acids. The appropriate expression systems of nucleic acids contain the DNA sequences necessary for expression in the patient.

The administration systems based on a bacterium involve the administration of a bacterium (such as Bacillus-Calmette-Guerrin) which expresses an immunogenic portion of the polypeptide at its surface. Preferably, the DNA can be introduced using a viral expression system (for example a pox virus, retrovirus or adenovirus) involving the use of (defective) non-pathogenic agents.

Although any appropriate carrier known to a person skilled in the art can be used in pharmaceutical compositions of this invention, the type of carrier will vary according to the chosen administration method. The compositions of the present invention can be formulated for each appropriate administration method, including, for example, the topical, nasal, intra-venous, intra-cranial, intra-peritoneal, sub-cutaneous and intramuscular routes.

For a parenteral administration, such as a sub-cutaneous injection, the carrier preferably contains water, salt, alcohol, fat, paraffin or a buffer. For oral administration, any carrier mentioned above or a solid carrier, such as mannitol, lactose, starch, magnesium stearate, talc, cellulose, glucose, sucrose and magnesium carbonate can be used. Biodegradable microspheres can also be used as carriers for the pharmaceutical compositions of this invention. For certain topical applications, formulations such as creams or lotions are preferred.

Such compositions can also comprise buffers (for example neutral or phosphate buffered saline solutions), carbohydrates (for example glucose, mannose, sucrose or dextrans), mannitol, proteins, polypeptides or amino acids such as glycine, antioxidants, chelating agents such as EDTA or glutathione, adjuvants (for example aluminium hydroxide) and/or protective agents. Alternatively, the compositions of the present invention can be presented in the form of a lyophilisate. Products can also be encapsulated in liposomes using standard technologies.

According to the invention, each of the varieties of adjuvant can be used in vaccines in order to induce the immune response. Most of the adjuvants contain a substance protecting the antigen from a rapid catabolism, such as aluminium hydroxide or mineral oil and an immune response stimulator such as lipid A, proteins derived from *Bordetella Pertussis* or *Mycobacteium tuberculosis*. Appropriate adjuvants are commercially available such as, for example: Freund's adjuvant and complete adjuvant (Difco Laboratories, Detroit, Mich., United States; Merck Adjuvant 65 (Merck and Company, Inc., Rahway, N.J., United States)), biodegradable microspheres; monophosphoryl lipid A; and cytokines such as GM-CSF or interleukin-2, -7 or -12.

The compositions described above can also be administered in the form of retard formulations (i.e. a formulation such as a capsule or a sponge which triggers the slow release of the product after administration). Such formulations can generally be prepared using technologies well known to a person skilled in the art and administered, for example, by oral, rectal route or sub-cutaneous implantation or implantation at the desired target site. The retard formulations can contain a polypeptide, a polynucleotide or an antibody dispersed in a carrier matrix and/or contained in a reservoir protected by a diffusion membrane. The carriers for the use of such formulations are biocompatible and must also be biodegradable; preferably the formulation provides a relatively constant level of release of the active component. The quantity of active product contained in the retard formulation depends on the implantation site.

Anticancer Therapy:

According to other features of the present invention, the products described can be used in anticancer therapy. In particular, the polynucleotides and polypeptides associated with the binding of human GHRH and being associated with the modulation of cell proliferation can be used in order to inhibit growth and induce the modulation of cell proliferation in tumours specific to the breast, the prostate or lung cancer.

Such polypeptides or polynucleotides can also be used for the therapy of numerous carcinomas including melanomas, the multiple forms of glioblastomas, carcinomas of the lung as well as colorectal cancers. Agents which activate the expression of such polypeptides or polynucleotides can also be used within the framework of these therapies.

According to these aspects of the invention, the products (which can be polypeptides or nucleic acids) are preferably incorporated into pharmaceutical compositions as described above.

Appropriate patients for the therapy are all warm-blooded animals, and preferably human beings. A patient eligible for a therapy according to the invention may or may not be diagnosed as affected by a cancer. In other words, the pharmaceutical compositions described above can thus be used in order to inhibit the development of a cancer at different stages of the disease (in order to prevent the appearance of a cancer or in order to treat a patient affected by a cancer).

The pharmaceutical compositions of the present invention are administered in a manner appropriate to each specific cancer to be treated.

The route, duration and frequency of administration are determined as a function of the state of the patient, type and severity of the disease, and administration method. The routes and frequencies of administration can vary from one individual to another. In general, the pharmaceutical compositions and the vaccines can be administered by injection (for example by intra-cutaneous, intramuscular, intravenous or sub-cutaneous route), by intra-nasal route (for example by inhalation) or by oral route. Preferably, between 1 and 10 doses can be administered over a 52-week period. Alternative protocols may be appropriate for each patient individually.

In general, an appropriate dosage and a treatment regime contains the active ingredient in a quantity sufficient to provide a therapeutic and/or prophylactic benefit. Such a response can be followed by the establishment of an improved clinical outlook (for example more frequent remissions, survival in the complete, partial or longer absence of the disease) in patients treated compared with patients not treated or treated with smaller doses.

According to other features of the present invention, a polypeptide can be administered in doses varying from 100 µg to 5 mg. The DNA molecules encoding for such polypeptides can be administered in a quantity sufficient to generate comparable polypeptide levels. Appropriate dosages can generally be determined using experimental models and/or clinical tests. In general, the use of the minimum dose sufficient to provide an effective therapy is preferred. The patients can generally be monitored with regard to the effectiveness of the therapy using tests appropriate to the conditions of treatment or prevention which will appear familiar to a person skilled in the art.

Unless otherwise defined, all the technical and scientific terms used here have the same meaning as that commonly understood by an ordinary specialist in the field to which this invention belongs. Similarly, all the publications, patent applications, all the patents and all other references mentioned here are incorporated by way of reference.

The following examples are presented in order to illustrate the above procedures and should in no case be considered as a limit to the scope of the invention.

EXAMPLES

Example 1

Cloning of the cDNA Encoding for Heterocarpine 1.1) Extraction of the RNAs from *Pilocarpus Heterophyllus* Cells:

The cells in culture are preserved at −80° C. before the stages of total RNA extraction. The total RNA extraction is based on a technique described in the scientific literature (Chomczynski and Sacchi, *Anal. Biochem.* (1987), 162, 156) using Trizol reagent (Gibco/BRL). The quality of the RNAs thus extracted is analyzed on 1% agarose gel in the presence of ethidium bromide.

1.2) Synthesis of the cDNAs by Reverse Transcription:

The RNAs are retrotranscribed according to two different operating methods in order to dissociate and promote the reverse transcriptions of the 5' and 3' parts of the RNAs using the SMART™ RACE cDNA Amplification Kit (Clontech).

1.3) Design and Synthesis of Primers for Polymerase Chain Reaction (PCR):

The amplification of the 2 sequences specific to the cDNA of heterocarpine was carried out by polymerase chain reaction (PCR) on reverse transcription products using the Rev1 primer for the products of 5' specific cDNA and the Fwd1 primer for the products of 3' specific cDNA of respective sequences SEQ. ID. NO. 4 and SEQ. ID. NO. 5.

The sequences SEQ. ID. NO. 4 and SEQ. ID. NO. 5 are the following:

SEQ. ID. NO. 4:
5'-TCC AAG CAG CAA AAA CTA GTG ACC CAG GGG CCA TTA TAT CT-3'

SEQ. ID. NO. 5:
5'-CGG TAT GGA CGC GGC TAT TGC TGA TGG TGT TGA TGT AA-3'

1.4) Polymerase Chain Reaction (PCR) and Results:

The reaction conditions include 0.2 µM of Fwd1 for the products of 3' specific cDNA and 0.2 µM of Rev1 for tee products of 5' specific cDNA, 200 µM dNTPs, 40 mM Tricine-KOH (pH 8.7), 15 mM KOAc, 3.5 mM Mg(Oac)$_2$, 3.75 g/ml BSA 0.005% Tween-20 (polyacetate), 0.005% Nonidet-P40, and 0.5 U Taq DNA polymerase in a final volume of 50 µl. The PCR reactions are carried out in a Perkin-Elmer 9700 thermocycler using the following thermal cycle parameters: 5 cycles comprising a denaturation at 94° C. for 5 seconds, a hybridization, of the primers at 72° C., 5 cycles comprising a denaturation at 94° C. for 5 seconds, a hybridization of the primers at 70° C. fix 10 seconds, and an extension of polymerization at 72° C. for 3 minutes and finally 25 cycles comprising a denaturation at 94° C. for 5 seconds, a hybridization of the primers at 68° C. for 10 seconds, and a polymerase extension at 72° C. for 3 minutes.

The products obtained by PCR are separated on 1% agarose gel and visualized using ethidium bromide staining.

The nucleic acid sequences of the products of 5' specific and 3' specific cDNA PCR are determined using an automatic sequencer. These are respectively the sequences SEQ. ID. NO. 6 and SEQ. ID. NO. 7 reproduced hereafter:

```
SEQ. ID. NO. 6:
   1 ctaatacgac tcactatagg gcaagcagtg gtatcaacgc agagtacgcg gggatgcccc
  61 aagctaattc ttatctttt tctttctttt tgttgttgtt ttgtcaaagc agcaatgagg
 121 tctaggaatg gtgttcttca tttattcctt ttcgttcttg catggcttct gttggcggct
 181 ctccatgcta actcaagttc ggatgagaga tcaacatata tagttcatat ggacaagacc
 241 catatgccca aaaccttctc tagcccccac cattggtact cttcggtcgt tcgatccctc
 301 aagtctacaa agccaaccaa attaaatcgc cgtcgatcct caccacttct tgtatactct
 361 tacgacaatg ctgctcatgg tttcagtgca gttttatctc aacaggaact tgaaactcta
 421 aaaaagtctc caggtttcgt ctcagtttat gccgataaga cagcgacact tgacaccacc
 481 catacacctg aatttctctc cctgaatact gccaacgggt tgtggcctgc ttcaaagtat
 541 ggtgaagata taattgttgg tgttattgac agcggtgtct ggccggagag tgaaagttat
 601 aatgatgatg gtatgggcgc tattccaagc agatggaagg gagaatgtga agctggacaa
 661 gagttcaatt cctccatgtg caactcaaag cttattggag ctagatattt cgataagggt
 721 atcattgcgg caaatcctgg gattaacatt agcatgaaat ctgccagaga tactatgggg
 781 catgggactc acacatcctc cacagttgct gggaattatg tggatggcgt ttcattcttt
 841 ggctatgcta aaggtacagc aaaaggagtg gcaccacggg cgagagtggc tatgtacaag
 901 gtcattttg acgaagggcg ctatgcatct gatgttcttg ccggtatgga cgcggctatt
 961 gctgatggtg ttgatgtaat ttcaatatca atgggatttg atgagacccc gttgtatgaa
1021 gatcctatag caattgcctc attcgctgct acagagaagg gcgtagtggt ctcatcttca
1081 gcaggaaatg cagggccagc gctagggagc ttgcacaatg gaatcccatg gacgttaact
1141 gttgcagctg gaaccattga ccgttcattt gcaggcacta taactcttgg gagtggggaa
1201 accatcattg gatggacaat gttcccagcc agtgcttatg tagcagactt gccactgctt
1261 tataacaaga cttactctgc atgcaactca actcgattat tatctcaact ccgaactgac
1321 gccatcatcg tatgcgaaga agctgaagat tcggtatctg agcaaatatc tgttgtcagt
1381 gcatcgaaca ttcggggagc catatttgtt tcagattatg atgctgaatt atttgaactt
1441 ggtggtgtga ctattcctgg tgtcgtgatt agcaccaagg atgcaccggc tgtgatcagc
1501 tacgccagca atgatgtgaa acctaaggca agcatcaagt tccaacaaac tgttctgggc
1561 acaaagcctg caccagccgt ggctttctat acttctagag gtccgtcacc gagctatcca
1621 ggcatcttaa agccagatat aatggcccct gggtcactag tttttgctgc ttgga
SEQ. ID. NO. 7:
   1 cggtatggac gcggctattg ctgatggtgt tgatgtaatt tcaatatcaa tgggatttga
  61 tgagacccg ttgtatgaag atcctatagc aattgcctca ttcgctgcta cagagaaggg
 121 cgtagtggtc tcatcttcag caggaaatgc agggccagcg ctagggagct tgcacaatgg
 181 aatcccatgg acgttaactg ttgcagctgg aaccattgac cgttcatttg caggcactat
 241 aactcttggg agtggggaaa ccatcattgg atggacaatg ttcccagcca gtgcttatgt
 301 agcagacttg ccactgcttt ataacaagac ttactctgca tgcaactcaa ctcgattatt
 361 atctcaactc cgaactgacg ccatcatcgt atgcgaagaa gctgaagatt cggtatctga
```

-continued

```
 421 gcaaatatct gttgtcagtg catcgaacat tcggggagcc atatttgttt cagattatga 481 tgctgaatta tttgaacttg gtggtgtgac tattcctggt gtcgtgatta gcaccaagga 541 tgcaccggct gtgatcagct acgccagcaa tgatgtgaaa cctaaggcaa gcatcaagtt 601 ccaacaaact gttctgggca caaagcctgc accagccgtg gctttctata cttctagagg 661 tccgtcaccg agctatccag gcatcttaaa gccagatata atggcccctg ggtcactagt 721 ttttgctgct tggattccaa atactgctac agcccaaatt ggtttgaata ccctcttgac 781 aagtgaatac aatatggttt ctggaacatc aatggcctgc cctcatgctg ctggtgtagc 841 tgctctcctt aagggcgcac accctgaatg gagtgcagct gctattaggt ctgcaatgat 901 gactacagca aatcccttgg ataacacact aaatccaatc cgggacaatg gtctaatcaa 961 tttcacatct gcttcacctt tagctatggg agccggccaa gttgatccta atcgggcact 1021 tgatcctggt ttgatttatg aaaccacccc acaagattat gtgagcctcc tctgcactct 1081 gaacttcacc caaaaccaaa tcctgtccat tacaagatca aaccgttaca gctgctccac 1141 ccctaatcct gatcttaact atccttcttt tattacttta cactacaaca caaatgcaac 1201 atttgttcag acttttcaca ggactgtgac taacgttgga ggaagcgcta caacttacaa 1261 ggccaagatc actgctcctc taggttctgt agttagtgtc tcaccagaca cattggcctt 1321 cagaaagcag tatgagcagc agagctacga gctcactatt gagtacaagc ctgatggtga 1381 agaaactgtt tcatttgggg aacttgtttg gattgaagaa aatgggaatc acactgtgag 1441 gagccctatt acagtgtcac cttccatgag taactttgtg tttatgggta cacaataatt 1501 gataaaaatt tgttctgatc acaactgtgg gaataatcga cgtttatgaa cccagaataa 1561 gttgtttggt cgtcttcaac attatcataa aggacttgaa tcatgtgtgt tgattttctg 1621 caaaaaaaaa aaaaaaaaaa aagtactctg cgttgatacc actgcttgcc ctatagtgag 1681 tcgtattag
```

The overlapping sequences SEQ. ID. NO. 6 and SEQ. ID. NO. 7 make it possible to deduce the complete sequence of the cDNA of sequence SEQ. ID. NO. 8 encoding for heterocarpine. The sequence SEQ. ID. NO. 8 is reproduced hereafter:

```
SEQ. ID. NO. 8:
   1 ctaatacgac tcactatagg gcaagcagtg gtatcaacgc agagtacgcg gggatgcccc 61 aagctaattc ttatcttttt tctttctttt tgttgttgtt ttgtcaaagc agcaatgagg 121 tctaggaatg gtgttcttca tttattcctt ttcgttcttg catggcttct gttggcggct 181 ctccatgcta actcaagttc ggatgagaga tcaacatata tagttcatat ggacaagacc 241 catatgccca aaaccttctc tagccccac cattggtact cttcggtcgt tcgatccctc 301 aagtctacaa agccaaccaa attaaatcgc cgtcgatcct caccacttct tgtatactct 361 tacgacaatg ctgctcatgg tttcagtgca gttttatctc aacaggaact tgaaactcta 421 aaaaagtctc caggtttcgt ctcagtttat gccgataaga cagcgacact tgacaccacc 481 catacacctg aatttctctc cctgaatact gccaacgggt tgtggcctgc ttcaaagtat 541 ggtgaagata taattgttgg tgttattgac agcggtgtct ggccggagag tgaaagttat 601 aatgatgatg gtatgggcgc tattccaagc agatggaagg gagaatgtga agctggacaa
```

```
 661 gagttcaatt cctccatgtg caactcaaag cttattggag ctagatattt cgataagggt
 721 atcattgcgg caaatcctgg gattaacatt agcatgaaat ctgccagaga tactatgggg
 781 catgggactc acacatcctc cacagttgct gggaattatg tggatggcgt ttcattcttt
 841 ggctatgcta aaggtacagc aaaaggagtg gcaccacggg cgagagtggc tatgtacaag
 901 gtcattttg acgaagggcg ctatgcatct gatgttcttg ccggtatgga cgcggctatt
 961 gctgatggtg ttgatgtaat ttcaatatca atgggatttg atgagacccc gttgtatgaa
1021 gatcctatag caattgcctc attcgctgct acagagaagg gcgtagtggt ctcatcttca
1081 gcaggaaatg cagggccagc gctagggagc ttgcacaatg gaatcccatg gacgttaact
1141 gttgcagctg gaaccattga ccgttcattt gcaggcacta taactcttgg gagtggggaa
1201 accatcattg gatggacaat gttcccagcc agtgcttatg tagcagactt gccactgctt
1261 tataacaaga cttactctgc atgcaactca actcgattat tatctcaact ccgaactgac
1321 gccatcatcg tatgcgaaga agctgaagat tcggtatctg agcaaatatc tgttgtcagt
1381 gcatcgaaca ttcggggagc catatttgtt tcagattatg atgctgaatt atttgaactt
1441 ggtggtgtga ctattcctgg tgtcgtgatt agcaccaagg atgcaccggc tgtgatcagc
1501 tacgccagca atgatgtgaa acctaaggca agcatcaagt tccaacaaac tgttctgggc
1561 acaaagcctg caccagccgt ggctttctat acttctagag gtccgtcacc gagctatcca
1621 ggcatcttaa agccagatat aatggcccct gggtcactag tttttgctgc ttggattcca
1681 aatactgcta cagcccaaat tggtttgaat accctcttga caagtaata caatatggtt
1741 tctggaacat caatggcctg ccctcatgct gctggtgtag ctgctctcct taagggcgca
1801 caccctgaat ggagtgcagc tgctattagg tctgcaatga tgactacagc aaatcccttg
1861 gataacacac taaatccaat ccgggacaat ggtctaatca atttcacatc tgcttcacct
1921 ttagctatgg gagccggcca agttgatcct aatcgggcac ttgatcctgg tttgatttat
1981 gaaaccaccc cacaagatta tgtgagcctc ctctgcactc tgaacttcac ccaaaaccaa
2041 atcctgtcca ttacaagatc aaaccgttac agctgctcca ccctaatcc tgatcttaac
2101 tatccttctt ttattacttt acactacaac acaaatgcaa catttgttca gacttttcac
2161 aggactgtga ctaacgttgg aggaagcgct acaacttaca aggccaagat cactgctcct
2221 ctaggttctg tagttagtgt ctcaccagac acattggcct tcagaaagca gtatgagcag
2281 cagagctacg agctcactat tgagtacaag cctgatggtg aagaaactgt ttcatttggg
2341 gaacttgttt ggattgaaga aaatgggaat cacactgtga ggagccctat tacagtgtca
2401 ccttccatga gtaactttgt gtttatgggt acacaataat tgataaaaat ttgttctgat
2461 cacaactgtg gaataatcg acgtttatga acccagaata agttgtttgg tcgtcttcaa
2521 cattatcata aaggacttga atcatgtgtg ttgattttct gcaaaaaaaa aaaaaaaaa
2581 aaagtactct gcgttgatac cactgcttgc cctatagtga gtcgtattag
```

In the sequence SEQ. ID. NO. 8, an open reading frame is observed in the presence of an initiation codon (ATG) encoding for an initiator methionine in position 115 and a stop codon (UAA) in position 2437. The polynucleotide containing the sequence encoding for heterocarpine corresponds to the sequence SEQ. ID. NO. 9, reproduced hereafter:

```
SEQ. ID. NO. 9:
  1 atgaggtcta ggaatggtgt tcttcattta ttccttttcg ttcttgcatg gcttctgttg
 61 gcggctctcc atgctaactc aagttcggat gagagatcaa catatatagt tcatatggac
```

```
 121 aagacccata tgcccaaaac cttctctagc ccccaccatt ggtactcttc ggtcgttcga 181 tccctcaagt ctacaaagcc aaccaaatta aatcgccgtc gatcctcacc acttcttgta 241 tactcttacg acaatgctgc tcatggtttc agtgcagttt tatctcaaca ggaacttgaa 301 actctaaaaa agtctccagg tttcgtctca gtttatgccg ataagacagc gacacttgac 361 accacccata cacctgaatt tctctccctg aatactgcca acgggttgtg gcctgcttca 421 aagtatggtg aagatataat tgttggtgtt attgacagcg gtgtctggcc ggagagtgaa 481 agttataatg atgatggtat gggcgctatt ccaagcagat ggaagggaga atgtgaagct 541 ggacaagagt tcaattcctc catgtgcaac tcaaagctta ttggagctag atatttcgat 601 aagggtatca ttgcggcaaa tcctgggatt aacattagca tgaaatctgc cagagatact 661 atggggcatg ggactcacac atcctccaca gttgctggga attatgtgga tggcgtttca 721 ttctttggct atgctaaagg tacagcaaaa ggagtggcac cacgggcgag agtggctatg 781 tacaaggtca tttttgacga agggcgctat gcatctgatg ttcttgccgg tatggacgcg 841 gctattgctg atggtgttga tgtaatttca atatcaatgg gatttgatga gaccccgttg 901 tatgaagatc ctatagcaat tgcctcattc gctgctacag agaagggcgt agtggtctca 961 tcttcagcag gaaatgcagg gccagcgcta gggagcttgc acaatggaat cccatggacg 1021 ttaactgttg cagctggaac cattgaccgt tcatttgcag gcactataac tcttgggagt 1081 ggggaaacca tcattggatg gacaatgttc ccagccagtg cttatgtagc agacttgcca 1141 ctgctttata caagactta ctctgcatgc aactcaactc gattattatc tcaactccga 1201 actgacgcca tcatcgtatg cgaagaagct gaagattcgg tatctgagca aatatctgtt 1261 gtcagtgcat cgaacattcg gggagccata tttgtttcag attatgatgc tgaattattt 1321 gaacttggtg gtgtgactat tcctggtgtc gtgattagca ccaaggatgc accggctgtg 1381 atcagctacg ccagcaatga tgtgaaacct aaggcaagca tcaagttcca acaaactgtt 1441 ctgggcacaa agcctgcacc agccgtggct ttctatactt ctagaggtcc gtcaccgagc 1501 tatccaggca tcttaaagcc agatataatg gcccctgggt cactagtttt tgctgcttgg 1561 attccaaata ctgctacagc ccaaattggt ttgaataccc tcttgacaag tgaatacaat 1621 atggtttctg gaacatcaat ggcctgccct catgctgctg gtgtagctgc tctccttaag 1681 ggcgcacacc ctgaatggag tgcagctgct attaggtctg caatgatgac tacagcaaat 1741 cccttggata acacactaaa tccaatccgg gacaatggtc taatcaattt cacatctgct 1801 tcacctttag ctatgggagc cggccaagtt gatcctaatc gggcacttga tcctggtttg 1861 atttatgaaa ccaccccaca agattatgtg agcctcctct gcactctgaa cttcacccaa 1921 aaccaaatcc tgtccattac aagatcaaac cgttacagct gctccacccc taatcctgat 1981 cttaactatc cttcttttat tactttacac tacaacacaa atgcaacatt tgttcagact 2041 tttcacagga ctgtgactaa cgttggagga agcgctacaa cttacaaggc caagatcact 2101 gctcctctag gttctgtagt tagtgtctca ccagacacat tggccttcag aaagcagtat 2161 gagcagcaga gctacgagct cactattgag tacaagcctg atggtgaaga aactgtttca 2221 tttgggggaac ttgtttggat tgaagaaaat gggaatcaca ctgtgaggag ccctattaca 2281 gtgtcacctt ccatgagtaa ctttgtgttt atgggtacac aataa
```

A protein of sequence SEQ. ID. NO. 10, composed of 774 amino acids and reproduced hereafter corresponds to the polynucleotide thus translated:

SEQ. ID. NO. 10:
```
  1 M R S R N G V L H L F L F V L A W L L L A A L H A N S S S D
 31 E R S T Y I V H M D K T H M P K T F S S P H H W Y S S V V R
 61 S L K S T K P T K L N R R R S S P L L V Y S Y D N A A H G F
 91 S A V L S Q Q E L E T L K K S P G F V S V Y A D K T A T L D
121 T T H T P E F L S L N T A N G L W P A S K Y G E D I I V G V
151 I D S G V W P E S E S Y N D D G M G A I P S R W K G E C E A
181 G Q E F N S S M C N S K L I G A R Y F D K G I I A A N P G I
211 N I S M K S A R D T M G H G T H T S S T V A G N Y V D G V S
241 F F G Y A K G T A K G V A P R A R V A M Y K V I F D E G R Y
271 A S D V L A G M D A A I A D G V D V I S I S M G F D E T P L
301 Y E D P I A I A S F A A T E K G V V V S S S A G N A G P A L
331 G S L H N G I P W T L T V A A G T I D R S F A G T I T L G S
361 G E T I I G W T M F P A S A Y V A D L P L L Y N K T Y S A C
391 N S T R L L S Q L R T D A I I V C E E A E D S V S E Q I S V
421 V S A S N I R G A I F V S D Y D A E L F E L G G V T I P G V
451 V I S T K D A P A V I S Y A S N D V K P K A S I K F Q Q T V
481 L G T K P A P A V A F Y T S R G P S P S Y P G I L K P D I M
511 A P G S L V F A A W I P N T A T A Q I G L N T L L T S E Y N
541 M V S G T S M A C P H A A G V A A L L K G A H P E W S A A A
571 I R S A M M T T A N P L D N T L N P I R D N G L I N F T S A
601 S P L A M G A G Q V D P N R A L D P G L I Y E T T P Q D Y V
631 S L L C T L N F T Q N Q I L S I T R S N R Y S C S T P N P D
661 L N Y P S F I T L H Y N T N A T F V Q T F H R T V T N V G G
691 S A T T Y K A K I T A P L G S V V S V S P D T L A F R K Q Y
721 E Q Q S Y E L T I E Y K P D G E E T V S F G E L V W I E E N
751 G N H T V R S P I T V S P S M S N F V F M G T Q
```

Example 2

Preparation of the Complete cDNA Encoding for Heterocarpine for Producing Recombinant Heterocarpine 2.1) Preparation of the RNAs from *Pilocarous Heterophyllus* Cell Culture:

The cells in culture are preserved at −80° C. before the stages of total RNA extraction. The total RNA extraction is based on a technique described in the scientific literature (Chomczynski and Sacchi, *Anal. Biochem*. (1987), 162, 156) using Trizol reagent (Gibco/BRL). The quality of the RNAs thus extracted is analyzed on 1% agarose gel in the presence of ethidium bromide.

2.2) Reverse Transcription from the RNAs:

The total RNAs are reverse transcribed with Oligo(dT) primers using Superscript® reverse transcriptase as suggested in the manufacturer's (Gibco/BRL) manual.

2.3) Polymerase Chain Reaction (PCR) on the Products Obtained from Reverse Transcription:

The amplification of the cDNA of heterocarpine was carried out by polymerase chain reaction (PCR) on the products of reverse transcription using the primers Fwd2 and Rev2 of respective sequences SEQ. ID. NO. 11 and SEQ. ID. NO. 12.

The sequences SEQ. ID. NO. 11 and SEQ. ID. NO. 12 are the following:

```
SEQ. ID. NO. 11:
5'-GGG GGA TCC GAG GTC TAG GAA TGG TGT TCT TCA-3'

SEQ. ID. NO. 12:
5'-GGG CTC GAG TTG TGT ACC CAT AAA CAC AAA GTT ACT
CAT GG-3'
```

The primer Fwd2 corresponds to the nucleotides 118 to 140 of SEQ. ID. NO. 8 and includes a BamH1 site (underlined) and three additional nucleotides in the 5' part in order to facilitate the cloning. The primer Rev2 corresponds to the sequence complementary to the region containing the nucleotides 2405 to 2436 of SEQ. ID. NO. 8 and includes an Xho1 site (underlined) and three additional nucleotides in the 5' part in order to facilitate the cloning.

The reaction conditions include 50 ng of the cDNA products of the reverse transcription reaction described above, 0.2 µM of Fwd2 (SEQ. ID. NO. 11) and of Rev2 (SEQ. ID. NO. 12), 200 µM dNTPs, 40 mM Tricine-KOH (pH 8.7), 15 mM KOAc, 3.5 mM Mg(Oac)$_2$, 3.75 µg/ml BSA, 0.005% Tween-20, 0.005% Nonidet-P40, and 0.5 U Taq DNA polymerase in a final volume of 50 µl. The PCR reactions are carried out in a Perkin-Elmer 9700 thermocycler using the following thermal cycle parameters: 5 cycles comprising a denaturation at 94° C. for 5 seconds, a hybridization of the primers at 72° C., 5 cycles comprising a denaturation at 94° C. for 5 seconds, a hybridization of the primers at 70° C. for 10 seconds, and a polymerase extension at 72° C. for 3 minutes and finally 25 cycles comprising a denaturation at 94° C. for 5 seconds, a hybridization of the primers at 68° C. for 10 seconds, and a polymerase extension at 72° C. for 3 minutes.

The products obtained by PCR are separated on 1% agarose gel and visualized using ethidium bromide staining. An approximately 2.3 kb band is obtained.

The nucleic acid sequence of the PCR product is verified using an automatic sequencer and corresponds to the sequence SEQ. ID. NO. 9 having artificially undergone deletion of the initiation codon ATG in order to allow the expression of recombinant heterocarpine from the pQE-TriSystem (Qiagen) phase vector with the BamH1 site as well as deletion of the stop codon in order to preserve the phase translation to protein and thus allow the synthesis of an 8× His sequence in the C-terminal region of heterocarpine. This sequence corresponds to the sequence SEQ. ID. NO. 13 reproduced hereafter:

```
SEQ. ID. NO. 13:
   1 gggggatccg aggtctagga atggtgttct tcatttattc cttttcgttc ttgcatggct
  61 tctgttggcg gctctccatg ctaactcaag ttcggatgag agatcaacat atatagttca
 121 tatggacaag acccatatgc ccaaaacctt ctctagcccc caccattggt actcttcggt
 181 cgttcgatcc ctcaagtcta caaagccaac caaattaaat cgccgtcgat cctcaccact
 241 tcttgtatac tcttacgaca atgctgctca tggtttcagt gcagttttat ctcaacagga
 301 acttgaaact ctaaaaaagt ctccaggttt cgtctcagtt tatgccgata agacagcgac
 361 acttgacacc acccatacac ctgaatttct ctccctgaat actgccaacg ggttgtggcc
 421 tgcttcaaag tatggtgaag atataattgt tggtgttatt gacagcggtg tctggccgga
 481 gagtgaaagt tataatgatg atggtatggg cgctattcca agcagatgga agggagaatg
 541 tgaagctgga caagagttca attcctccat gtgcaactca aagcttattg gagctagata
 601 tttcgataag ggtatcattg cggcaaatcc tgggattaac attagcatga aatctgccag
 661 agatactatg gggcatggga ctcacacatc ctccacagtt gctgggaatt atgtggatgg
 721 cgtttcattc tttggctatg ctaaaggtac agcaaaagga gtggcaccac gggcgagagt
 781 ggctatgtac aaggtcattt ttgacgaagg gcgctatgca tctgatgttc ttgccggtat
 841 ggacgcggct attgctgatg gtgttgatgt aatttcaata tcaatgggat ttgatgagac
 901 cccgttgtat gaagatccta tagcaattgc ctcattcgct gctacagaga agggcgtagt
 961 ggtctcatct tcagcaggaa atgcagggcc agcgctaggg agcttgcaca atggaatccc
1021 atggacgtta actgttgcag ctggaaccat tgaccgttca tttgcaggca ctataactct
1081 tgggagtggg gaaaccatca ttggatggac aatgttccca gccagtgctt atgtagcaga
1141 cttgccactg ctttataaca agacttactc tgcatgcaac tcaactcgat tattatctca
1201 actccgaact gacgccatca tcgtatgcga agaagctgaa gattcggtat ctgagcaaat
1261 atctgttgtc agtgcatcga acattcgggg agccatattt gtttcagatt atgatgctga
1321 attatttgaa cttggtggtg tgactattcc tggtgtcgtg attagcacca aggatgcacc
1381 ggctgtgatc agctacgcca gcaatgatgt gaaacctaag gcaagcatca agttccaaca
1441 aactgttctg ggcacaaagc ctgcaccagc cgtggctttc tatacttcta gaggtccgtc
1501 accgagctat ccaggcatct aaagccaga tataatggcc cctgggtcac tagttttgc
1561 tgcttggatt ccaaatactg ctacagccca aattggtttg aataccctct tgacaagtga
1621 atacaatatg gtttctggaa catcaatggc ctgccctcat gctgctggtg tagctgctct
1681 ccttaagggc gcacaccctg aatggagtgc agctgctatt aggtctgcaa tgatgactac
```

```
                       -continued
1741 agcaaatccc ttggataaca cactaaatcc aatccgggac aatggtctaa tcaatttcac 1801 atctgcttca cctttagcta tgggagccgg ccaagttgat cctaatcggg cacttgatcc 1861 tggtttgatt tatgaaacca ccccacaaga ttatgtgagc ctcctctgca ctctgaactt 1921 cacccaaaac caaatcctgt ccattacaag atcaaaccgt tacagctgct ccacccctaa 1981 tcctgatctt aactatcctt cttttattac tttacactac aacacaaatg caacatttgt 2041 tcagacttt cacaggactg tgactaacgt tggaggaagc gctacaactt acaaggccaa 2101 gatcactgct cctctaggtt ctgtagttag tgtctcacca gacacattgg ccttcagaaa 2161 gcagtatgag cagcagagct acgagctcac tattgagtac aagcctgatg gtgaagaaac 2221 tgtttcattt ggggaacttg tttggattga agaaaatggg aatcacactg tgaggagccc 2281 tattacagtg tcaccttcca tgagtaactt tgtgtttatg ggtacacaac tcgagccc
```

This sequence encodes for a protein of sequence SEQ. ID. NO. 14 reproduced hereafter:

```
  1M A I S R E L V D P R S R N G V L H L F L F V L A W L L L A
 31A L H A N S S S D E R S T Y I V H M D K T H M P K T F S S P
 61H H W Y S S V V R S L K S T K P T K L N R R R S S P L L V Y
 91S Y D N A A H G F S A V L S Q Q E L E T L K K S P G F V S V
121Y A D K T A T L D T T H T P E F L S L N T A N G L W P A S K
151Y G E D I I V G V I D S G V W P E S E S Y N D D G M G A I P
181S R W K G E C E A G Q E F N S S M C N S K L I G A R Y F D K
211G I I A A N P G I N I S M K S A R D T M G H G T H T S S T V
241A G N Y V D G V S F F G Y A K G T A K G V A P R A R V A M Y
271K V I F D E G R Y A S D V L A G M D A A I A D G V D V I S I
301S M G F D E T P L Y E D P I A I A S F A A T E K G V V V S S
331S A G N A G P A L G S L H N G I P W T L T V A A G T I D R S
361F A G T I T L G S G E T I I G W T M F P A S A Y V A D L P L
391L Y N K T Y S A C N S T R L L S Q L R T D A I I V C E E A E
421D S V S E Q I S V V S A S N I R G A I F V S D Y D A E L F E
451L G G V T I P G V V I S T K D A P A V I S Y A S N D V K P K
481A S I K F Q Q T V L G T K P A P A V A F Y T S R G P S P S Y
511P G I L K P D I M A P G S L V F A A W I P N T A T A Q I G L
541N T L L T S E Y N M V S G T S M A C P H A A G V A A L L K G
571A H P E W S A A A I R S A M M T T A N P L D N T L N P I R D
601N G L I N F T S A S P L A M G A G Q V D P N R A L D P G L I
631Y E T T P Q D Y V S L L C T L N F T Q N Q I L S I T R S N R
661Y S C S T P N P D L N Y P S F I T L H Y N T N A T F V Q T F
691H R T V T N V G G S A T T Y K A K I T A P L G S V V S V S P
721D T L A F R K Q Y E Q Q S Y E L T I E Y K P D G E E T V S F
751G E L V W I E E N G N H T V R S P I T V S P S M S N F V F M
781G T Q L E H H H H H H H H
```

Example 3

Production of Recombinant Heterocarpine by Bacteria

The part of the cDNA encoding for heterocarpine is inserted at the BamH1/Xho1 sites of the pQE-TriSystem (Qiagen) expression vector and is expressed using *E. coli* M15 bacteria as host bacteria. 20 ml of LB medium containing 100 μg/ml of ampicillin and 25 μg/ml of kanamycin are inoculated and the bacteria brought to 37° C. under stirring for 12 hours. From this culture, 1 litre of LB medium containing 100 μg/ml of ampicillin and 25 μg/ml of kanamycin is inoculated and the bacteria are stirred at 37° C. until an optical density of 0.6 at 600 nm is obtained.

The expression of the recombinant heterocarpine is produced by the addition of IPTG at a final concentration of 1 mM over 4 to 5 hours. The bacteria are then recovered by centrifugation at 4000×g for 20 minutes then frozen in liquid nitrogen. The pellet is then thawed in ice for 15 minutes and suspended in a pH 8.0 lysis buffer composed of 50 mM $NaH_2PO_4$, 300 mM NaCl and 10 mM imidazole in the presence of 1 mg/ml of lysozyme for 30 minutes in ice. The lysis is finally completed by a sonication stage and the debris eliminated by centrifugation. The lysate (4 ml) thus clarified is mixed with 1 ml of a nickel matrix suspension and stirred at 4° C. for 60 minutes. All of the reaction medium is placed in a column, washed in the presence of 50 mM $NaH_2PO_4$, 300 mM NaCl and 20 mM imidazole. The heterocarpine is finally eluted with 4×0.5 ml of buffer constituted by 50 mM $NaH_2PO_4$, 300 mM NaCl and 250 mM imidazole.

Example 4

Production of Recombinant Heterocarpine by Cells from Insects Infected by the Baculovirus The part of the cDNA encoding for heterocarpine is inserted at the BamH1/Xho1 sites of the pQE-TriSystem (Qiagen) expression vector. The pQE-TriSystem vector contains the viral sequences of *Autographa california* nuclear polyhedrosis virus (AcNPV) allowing homologous recombination. The recombinant baculovirus containing the heterocarpine sequence is prepared by co-transfection of the pQE-TriSystem vector with the genomic linearized DNA of the baculovirus in sf9 or sf21 insect cells established from ovarian tissues of the *Spodoptera frugiperda* larva. The transfected cells are washed with phosphate buffer and collected by centrifugation at 1000×g for 5 minutes. The pellet is suspended in a pH 8.0 lysis buffer composed of 50 mM $NaH_2PO_4$, 300 mM NaCl and 10 mM imidazole. The lysis is finally completed by a sonication stage and the debris eliminated by centrifugation. The lysate (4 ml) thus clarified is mixed with 200 μl of a nickel matrix suspension and stirred at 4° C. for 60 minutes. All of the reaction medium is placed in a column, washed in the presence of 50 mM $NaH_2PO_4$, 300 mM NaCl and 20 mM imidazole. The heterocarpine is finally eluted with 4×0.5 ml of buffer constituted by 50 mM $NaH_2PO_4$, 300 mM NaCl and 250 mM imidazole.

Example 5

Production of Recombinant Heterocarpine by Mammal Cells

The part of the cDNA encoding for heterocarpine is inserted at the BamH1/Xho1 sites of the pQE-TriSystem (Qiagen) expression vector. The pQE-TriSystem vector contains the activating sequences of the cytomegalovirus (CMV) fused to chicken beta-actin promoter allowing a very significant heterologous expression. Human embryo kidney (HEK-293) cells are cultured in DMEM medium (Dulbecco'S Modified Eagle's Medium) containing 100 U/ml of penicillin and 100 μg/ml of streptomycin sulphate, complemented with 10% foetal calf serum. The cells are sub-cultured 24 hours before the transfection protocol allowing normal metabolism of the cells and better transfection efficiency. The transfection of 1 μg of pQE-TriSystem containing the cDNA encoding for heterocarpine was carried out using Effectene® Transfection reagent according to the manufacturer's (Qiagen) recommendations.

The transfected cells are washed with phosphate buffer and collected by centrifugation at 1000×g for 5 minutes. The pellet is suspended in a pH 8.0 lysis buffer composed of 50 mM $NaH_2PO_4$, 300 mM NaCl, 10 mM imidazole in the presence of 0.05% Tween® 20. The lysis is finally completed by a sonication stage and the debris eliminated by centrifugation. The lysate (4 ml) thus clarified is mixed with 200 μl of a nickel matrix suspension and stirred at 4° C. for 60 minutes. All of the reaction medium is placed in a column, washed in the presence of 50 mM $NaH_2PO_4$, 300 mM NaCl and 20 mM imidazole. The heterocarpine is finally eluted with 4×0.5 ml of buffer constituted by 50 mM $NaH_2PO_4$, 300 mM NaCl and 250 mM imidazole.

Example 6

Measurement of the Binding to the Human GHRH Receptor

Stable Transfections of the Human GHRH Receptor (hGHRH-R):

HEK-293 human embryo kidney cells (a cell line developed by Dr. Stuart Sealfon, Mount Sinai Medical School, New York, N.Y.) expressing the human GHRH receptor in stable manner were obtained from Dr. Kelly Mayo (Northwestern University, Chicago, Ill.).

Cell Culture and Membrane Preparation:

The HEK-293 cells transfected in a stable manner with the human GHRH receptor described above are cultured in DMEM (Dulbecco's Modified Eagle's Medium, high glucose content; supplied by Life technologies) supplemented with 0.4 mg/ml of G418 (Life technologies) in the presence of 10% foetal calf serum and 4 mM of L-glutamine (Life Technologies). The cells are homogenized in buffer A containing 50 mM HEPES (pH 7.4), 5 mM of magnesium chloride ($MgCl_2$), 2 mM of ethyleneglycol-bis(2-amino-ethyl)-N,N, N',N'-tetraacetic acid (EGTA) and 50 μg/ml of bacitracin then subjected to sonication in the same buffer A. The cells thus homogenized are centrifuged at 4° C. at 39,000 g for 10 minutes, suspended in the buffer A and re-centrifuged at 4° C. at 40,000 g for 10 minutes. The total membrane proteins are quantified by Bradford's technique. The pelleted membranes are thus stored at −80° C. for later use.

Competitive Binding Test on hGHRH-R:

The membranes of the HEK-293 cells transfected in a stable manner with the human GHRH receptor are diluted to a concentration of 100 μg/ml in reaction buffer containing 50 mM HEPES (pH 7.4), 5 mM of $MgCl_2$, 2 mM of EGTA, 50 μg/ml of bacitracin and 0.5% bovine serum albumin (BSA). The membranes are incubated with 0.05 nM of [$^{125}$I]GHRH (1-44 amide) (Amersham) in a final volume of 200 µl in the presence of increasing concentrations of heterocarpine for 2 hours at 23° C. The reaction is stopped by rapid filtration on GF/C 96-well filters 0.1% pre-loaded with polyethylenimine. The filters are then washed three times at 4° C. with washing buffer containing 50 mM Tris (pH 7.4) using a Packard 96-well filtration station. The filters thus dried are submerged in 20 µl of scintillation cocktail (Microscint O, Packard) and are subjected to counting by Topcount (Packard). The non-specific activity is determined in the presence of 100 nM of hGHRH. A dose-response curve is generated for hGHRH (0.001 nM-100 nM) and makes it possible to determine the inhibitory concentration $IC_{50}$ of protein/polypeptide at which 50% human GHRH does not bind to human GHRH receptor.

```
                         SEQUENCE LISTING

<160> NUMBER OF SEQ ID NOS: 14

<210> SEQ ID NO 1
<211> LENGTH: 10
<212> TYPE: PRT
<213> ORGANISM: Pilocarpus Heterophyllus (peptide fragment)

<400> SEQUENCE: 1

Lys Leu Ile Gly Ala Arg Tyr Phe Asp Lys
1               5                   10

<210> SEQ ID NO 2
<211> LENGTH: 14
<212> TYPE: PRT
<213> ORGANISM: Pilocarpus Heterophyllus (peptide fragment)

<400> SEQUENCE: 2

Tyr Gly Glu Asp Ile Ile Val Gly Val Ile Asp Ser Gly Val
1               5                   10

<210> SEQ ID NO 3
<211> LENGTH: 6
<212> TYPE: PRT
<213> ORGANISM: Pilocarpus Heterophyllus (peptide fragment)

<400> SEQUENCE: 3

Pro Glu Ser Glu Ser Tyr
1               5

<210> SEQ ID NO 4
<211> LENGTH: 41
<212> TYPE: DNA
<213> ORGANISM: Artificial Sequence
<220> FEATURE:
<223> OTHER INFORMATION: Primer for 5' specific cDNA products

<400> SEQUENCE: 4
tccaagcagc aaaaactagt gacccagggg ccattatatc t                    41

<210> SEQ ID NO 5
<211> LENGTH: 38
<212> TYPE: DNA
<213> ORGANISM: Artificial Sequence
<220> FEATURE:
<223> OTHER INFORMATION: Primer for 3' specific cDNA products

<400> SEQUENCE: 5
cggtatggac gcggctattg ctgatggtgt tgatgtaa                        38

<210> SEQ ID NO 6
<211> LENGTH: 1675
<212> TYPE: DNA
<213> ORGANISM: Pilocarpus Heterophyllus (5' cDNA fragment of the cDNA
      encoding for heterocarpine)

<400> SEQUENCE: 6
```

-continued

```
ctaatacgac tcactatagg gcaagcagtg gtatcaacgc agagtacgcg gggatgcccc      60
aagctaattc ttatctttt  tctttcttt  tgttgttgtt  ttgtcaaagc agcaatgagg    120
tctaggaatg gtgttcttca tttattcctt ttcgttcttg catggcttct gttggcggct    180
ctccatgcta actcaagttc ggatgagaga tcaacatata tagttcatat ggacaagacc    240
catatgccca aaaccttctc tagcccccac cattggtact cttcggtcgt tcgatccctc    300
aagtctacaa agccaaccaa attaaatcgc cgtcgatcct caccacttct tgtatactct    360
tacgacaatg ctgctcatgg tttcagtgca gttttatctc aacaggaact tgaaactcta    420
aaaaagtctc caggtttcgt ctcagtttat gccgataaga cagcgacact tgacaccacc    480
catacacctg aatttctctc cctgaatact gccaacgggt tgtggcctgc ttcaaagtat    540
ggtgaagata taattgttgg tgttattgac agcggtgtct ggccggagag tgaaagttat    600
aatgatgatg gtatgggcgc tattccaagc agatggaagg gagaatgtga agctggacaa    660
gagttcaatt cctccatgtg caactcaaag cttattggag ctagatattt cgataagggt    720
atcattgcgg caaatcctgg gattaacatt agcatgaaat ctgccagaga tactatgggg    780
catgggactc acacatcctc cacagttgct gggaattatg tggatggcgt ttcattcttt    840
ggctatgcta aggtacagc  aaaaggagtg gcaccacggg cgagagtggc tatgtacaag    900 gtcattttg  acgaagggcg ctatgcatct gatgttcttg ccggtatgga cgcggctatt    960
gctgatggtg ttgatgtaat ttcaatatca atgggatttg atgagacccc gttgtatgaa   1020
gatcctatag caattgcctc attcgctgct acagagaagg gcgtagtggt ctcatcttca   1080
gcaggaaatg cagggccagc gctagggagc ttgcacaatg gaatcccatg gacgttaact   1140
gttgcagctg gaaccattga ccgttcattt gcaggcacta taactcttgg gagtgggaa   1200 accatcattg gatggacaat gttcccagcc agtgcttatg tagcagactt gccactgctt   1260
tataacaaga cttactctgc atgcaactca actcgattat tatctcaact ccgaactgac   1320
gccatcatcg tatgcgaaga agctgaagat tcggtatctg agcaaatatc tgttgtcagt   1380
gcatcgaaca ttcggggagc catatttgtt tcagattatg atgctgaatt atttgaactt   1440
ggtggtgtga ctattcctgg tgtcgtgatt agcaccaagg atgcaccggc tgtgatcagc   1500
tacgccagca atgatgtgaa acctaaggca agcatcaagt tccaacaaac tgttctgggc   1560
acaaagcctg caccagccgt ggctttctat acttctagag gtccgtcacc gagctatcca   1620
ggcatcttaa agccagatat aatggcccct gggtcactag ttttgctgc  ttgga        1675
```

<210> SEQ ID NO 7
<211> LENGTH: 1689
<212> TYPE: DNA
<213> ORGANISM: Pilocarpus Heterophyllus (3' cDNA fragment of the cDNA encoding for heterocarpine)

<400> SEQUENCE: 7

```
cggtatggac gcggctattg ctgatggtgt tgatgtaatt tcaatatcaa tgggatttga     60
tgagaccccg ttgtatgaag atcctatagc aattgcctca ttcgctgcta cagagaaggg    120
cgtagtggtc tcatcttcag caggaaatgc agggccagcg ctagggagct tgcacaatgg    180
aatcccatgg acgttaactg ttgcagctgg aaccattgac cgttcatttg caggcactat    240
aactcttggg agtggggaaa ccatcattgg atggacaatg ttcccagcca gtgcttatgt    300
agcagacttg ccactgcttt ataacaagac ttactctgca tgcaactcaa ctcgattatt    360
atctcaactc cgaactgacg ccatcatcgt atgcgaagaa gctgaagatt cggtatctga    420
```

-continued

```
gcaaatatct gttgtcagtg catcgaacat tcggggagcc atatttgttt cagattatga      480
tgctgaatta tttgaacttg gtggtgtgac tattcctggt gtcgtgatta gcaccaagga      540
tgcaccggct gtgatcagct acgccagcaa tgatgtgaaa cctaaggcaa gcatcaagtt      600
ccaacaaact gttctgggca caaagcctgc accagccgtg gctttctata cttctagagg      660
tccgtcaccg agctatccag gcatcttaaa gccagatata atggcccctg ggtcactagt      720
ttttgctgct tggattccaa atactgctac agcccaaatt ggtttgaata ccctcttgac      780
aagtgaatac aatatggttt ctggaacatc aatggcctgc cctcatgctg ctggtgtagc      840
tgctctcctt aagggcgcac accctgaatg gagtgcagct gctattaggt ctgcaatgat      900
gactacagca atcccttgg ataacacact aaatccaatc cgggacaatg gtctaatcaa      960
tttcacatct gcttcacctt tagctatggg agccggccaa gttgatccta atcgggcact      1020
tgatcctggt ttgatttatg aaaccacccc acaagattat gtgagcctcc tctgcactct      1080
gaacttcacc caaaaccaaa tcctgtccat tacaagatca aaccgttaca gctgctccac      1140
ccctaatcct gatcttaact atccttcttt tattactta cactacaaca caaatgcaac      1200
atttgttcag acttttcaca ggactgtgac taacgttgga ggaagcgcta caacttacaa      1260
ggccaagatc actgctcctc taggttctgt agttagtgtc tcaccagaca cattggcctt      1320
cagaaagcag tatgagcagc agagctacga gctcactatt gagtacaagc tgatggtga      1380 agaaactgtt tcatttgggg aacttgtttg gattgaagaa atgggaatc acactgtgag      1440 gagccctatt acagtgtcac cttccatgag taactttgtg tttatgggta cacaataatt      1500
gataaaaatt tgttctgatc acaactgtgg gaataatcga cgtttatgaa cccagaataa      1560
gttgtttggt cgtcttcaac attatcataa aggacttgaa tcatgtgtgt tgattttctg      1620
caaaaaaaaa aaaaaaaaaa aagtactctg cgttgatacc actgcttgcc ctatagtgag      1680
tcgtattag                                                              1689
```

<210> SEQ ID NO 8
<211> LENGTH: 2630
<212> TYPE: DNA
<213> ORGANISM: Pilocarpus Heterophyllus (cDNA encoding for heterocarpine)

<400> SEQUENCE: 8

```
ctaatacgac tcactatagg gcaagcagtg gtatcaacgc agagtacgcg gggatgcccc      60
aagctaattc ttatctttt tctttctttt tgttgttgtt ttgtcaaagc agcaatgagg      120
tctaggaatg gtgttcttca tttattcctt ttcgttcttg catggcttct gttggcggct      180
ctccatgcta actcaagttc ggatgagaga tcaacatata tagttcatat ggacaagacc      240
catatgccca aaaccttctc tagccccac cattggtact cttcggtcgt tcgatccctc       300
aagtctacaa agccaaccaa attaaatcgc cgtcgatcct caccacttct tgtatactct      360
tacgacaatg ctgctcatgg tttcagtgca gttttatctc aacaggaact tgaaactcta      420
aaaaagtctc caggtttcgt ctcagtttat gccgataaga cagcgacact tgacaccacc      480
catacacctg aatttctctc cctgaatact gccaacgggt tgtggcctgc ttcaaagtat      540
ggtgaagata taattgttgg tgttattgac agcggtgtct ggccgagag tgaaagttat       600 aatgatgatg gtatgggcgc tattccaagc agatggaagg gagaatgtga agctggacaa      660
gagttcaatt cctccatgtg caactcaaag cttattggag ctagatattt cgataagggt      720
atcattgcgg caaatcctgg gattaacatt agcatgaaat ctgccagaga tactatgggg      780
```

```
catgggactc acacatcctc cacagttgct gggaattatg tggatggcgt ttcattcttt    840
ggctatgcta aggtacagc aaaaggagtg gcaccacggg cgagagtggc tatgtacaag    900 gtcattttg acgaagggcg ctatgcatct gatgttcttg ccggtatgga cgcggctatt    960
gctgatggtg ttgatgtaat ttcaatatca atgggatttg atgagacccc gttgtatgaa   1020
gatcctatag caattgcctc attcgctgct acagagaagg gcgtagtggt ctcatcttca   1080
gcaggaaatg cagggccagc gctagggagc ttgcacaatg gaatcccatg gacgttaact   1140
gttgcagctg gaaccattga ccgttcattt gcaggcacta taactcttgg gagtggggaa   1200
accatcattg gatggacaat gttcccagcc agtgcttatg tagcagactt gccactgctt   1260
tataacaaga cttactctgc atgcaactca actcgattat tatctcaact ccgaactgac   1320
gccatcatcg tatgcgaaga agctgaagat tcggtatctg agcaaatatc tgttgtcagt   1380
gcatcgaaca ttcggggagc catatttgtt tcagattatg atgctgaatt atttgaactt   1440
ggtggtgtga ctattcctgg tgtcgtgatt agcaccaagg atgcaccggc tgtgatcagc   1500
tacgccagca atgatgtgaa acctaaggca agcatcaagt tccaacaaac tgttctgggc   1560
acaaagcctg caccagccgt ggctttctat acttctagag gtccgtcacc gagctatcca   1620
ggcatcttaa agccagatat aatgcccct gggtcactag tttttgctgc ttggattcca   1680
aatactgcta cagcccaaat tggtttgaat accctcttga caagtgaata caatatggtt   1740
tctggaacat caatggcctg ccctcatgct gctggtgtag ctgctctcct taagggcgca   1800
caccctgaat ggagtgcagc tgctattagg tctgcaatga tgactacagc aaatcccttg   1860
gataacacac taaatccaat ccgggacaat ggtctaatca atttcacatc tgcttcacct   1920
ttagctatgg gagccggcca agttgatcct aatcgggcac ttgatcctgg tttgatttat   1980
gaaaccaccc cacaagatta tgtgagcctc ctctgcactc tgaacttcac ccaaaaccaa   2040
atcctgtcca ttcaagatc aaaccgttac agctgctcca ccctaatcc tgatcttaac   2100 tatccttctt ttattacttt acactacaac acaaatgcaa catttgttca gacttttcac   2160
aggactgtga ctaacgttgg aggaagcgct acaacttaca aggccaagat cactgctcct   2220
ctaggttctg tagttagtgt ctcaccagac acattggcct tcagaaagca gtatgagcag   2280
cagagctacg agctcactat tgagtacaag cctgatggtg aagaaactgt ttcatttggg   2340
gaacttgttt ggattgaaga aaatgggaat cacactgtga ggagccctat tacagtgtca   2400
ccttccatga gtaactttgt gtttatgggt acacaataat tgataaaaat ttgttctgat   2460
cacaactgtg gaataatcg acgtttatga acccagaata agttgtttgg tcgtcttcaa   2520
cattatcata aaggacttga atcatgtgtg ttgattttct gcaaaaaaaa aaaaaaaaa    2580 aaagtactct gcgttgatac cactgcttgc cctatagtga gtcgtattag                2630
```

<210> SEQ ID NO 9
<211> LENGTH: 2325
<212> TYPE: DNA
<213> ORGANISM: Pilocarpus Heterophyllus (encoding part of cDNA encoding for heterocarpine)

<400> SEQUENCE: 9

```
atgaggtcta ggaatggtgt tcttcattta ttccttttcg ttcttgcatg gcttctgttg     60
gcggctctcc atgctaactc aagttcggat gagagatcaa catatatagt tcatatggac   120
aagacccata tgcccaaaac cttctctagc ccccaccatt ggtactcttc ggtcgttcga   180
tccctcaagt ctacaaagcc aaccaaatta atcgccgtc gatcctcacc acttcttgta    240
```

```
tactcttacg acaatgctgc tcatggtttc agtgcagttt tatctcaaca ggaacttgaa    300
actctaaaaa agtctccagg tttcgtctca gtttatgccg ataagacagc gacacttgac    360
accacccata cacctgaatt tctctccctg aatactgcca acggttgtg gcctgcttca     420 aagtatggtg aagatataat tgttggtgtt attgacagcg gtgtctggcc ggagagtgaa    480
agttataatg atgatggtat gggcgctatt ccaagcagat ggaagggaga atgtgaagct    540
ggacaagagt tcaattcctc catgtgcaac tcaaagctta ttggagctag atatttcgat    600
aagggtatca ttgcggcaaa tcctgggatt aacattagca tgaaatctgc cagagatact    660
atggggcatg ggactcacac atcctccaca gttgctggga attatgtgga tggcgtttca    720
ttctttggct atgctaaagg tacagcaaaa ggagtggcac cacgggcgag agtggctatg    780
tacaaggtca tttttgacga agggcgctat gcatctgatg ttcttgccgg tatggacgcg    840
gctattgctg atggtgttga tgtaatttca atatcaatgg gatttgatga accccgttg    900 tatgaagatc ctatagcaat tgcctcattc gctgctacag agaagggcgt agtggtctca    960
tcttcagcag gaaatgcagg gccagcgcta gggagcttgc acaatggaat cccatggacg   1020
ttaactgttg cagctggaac cattgaccgt tcatttgcag gcactataac tcttgggagt   1080
ggggaaacca tcattggatg gacaatgttc ccagccagtg cttatgtagc agacttgcca   1140
ctgctttata acaagactta ctctgcatgc aactcaactc gattattatc tcaactccga   1200
actgacgcca tcatcgtatg cgaagaagct gaagattcgg tatctgagca aatatctgtt   1260
gtcagtgcat cgaacattcg gggagccata tttgtttcag attatgatgc tgaattattt   1320
gaacttggtg gtgtgactat tcctggtgtc gtgattagca ccaaggatgc accggctgtg   1380
atcagctacg ccagcaatga tgtgaaacct aaggcaagca tcaagttcca acaaactgtt   1440
ctgggcacaa agcctgcacc agccgtggct ttctatactt ctagaggtcc gtcaccgagc   1500
tatccaggca tcttaaagcc agatataatg gcccctgggt cactagtttt tgctgcttgg   1560
attccaaata ctgctacagc ccaaattggt ttgaataccc tcttgacaag tgaatacaat   1620
atggtttctg aacatcaat ggcctgccct catgctgctg gtgtagctgc tctccttaag    1680
ggcgcacacc ctgaatggag tgcagctgct attaggtctg caatgatgac tacagcaaat   1740
cccttggata cacactaaa tccaatccgg acaatggtc taatcaattt cacatctgct    1800
tcacctttag ctatgggagc cggccaagtt gatcctaatc gggcacttga tcctggtttg   1860
atttatgaaa ccaccccaca agattatgtg agcctcctct gcactctgaa cttcacccaa   1920
aaccaaatcc tgtccattac aagatcaaac cgttacagct gctccacccc taatcctgat   1980
cttaactatc cttcttttat tactttacac tacaacacaa atgcaacatt tgttcagact   2040
tttcacagga ctgtgactaa cgttggagga agcgctacaa cttacaaggc caagatcact   2100
gctcctctag gttctgtagt tagtgtctca ccagacacat tggccttcag aaagcagtat   2160
gagcagcaga gctacgagct cactattgag tacaagcctg atggtgaaga aactgtttca   2220
tttggggaac ttgtttggat tgaagaaaat gggaatcaca ctgtgaggag ccctattaca   2280
gtgtcaccct tccatgagta actttgtgttt atgggtacac aataa                  2325
```

<210> SEQ ID NO 10
<211> LENGTH: 774
<212> TYPE: PRT
<213> ORGANISM: Pilocarpus Heterophyllus (heterocarpine)

<400> SEQUENCE: 10

```
Met Arg Ser Arg Asn Gly Val Leu His Leu Phe Leu Phe Val Leu Ala
1               5                   10                  15

Trp Leu Leu Leu Ala Ala Leu His Ala Asn Ser Ser Ser Asp Glu Arg
            20                  25                  30

Ser Thr Tyr Ile Val His Met Asp Lys Thr His Met Pro Lys Thr Phe
        35                  40                  45

Ser Ser Pro His His Trp Tyr Ser Ser Val Val Arg Ser Leu Lys Ser
    50                  55                  60

Thr Lys Pro Thr Lys Leu Asn Arg Arg Ser Ser Pro Leu Leu Val
65              70                  75                  80

Tyr Ser Tyr Asp Asn Ala Ala His Gly Phe Ser Ala Val Leu Ser Gln
                85                  90                  95

Gln Glu Leu Glu Thr Leu Lys Lys Ser Pro Gly Phe Val Ser Val Tyr
                100                 105                 110

Ala Asp Lys Thr Ala Thr Leu Asp Thr Thr His Thr Pro Glu Phe Leu
            115                 120                 125

Ser Leu Asn Thr Ala Asn Gly Leu Trp Pro Ala Ser Lys Tyr Gly Glu
        130                 135                 140

Asp Ile Ile Val Gly Val Ile Asp Ser Gly Val Trp Pro Glu Ser Glu
145                 150                 155                 160

Ser Tyr Asn Asp Asp Gly Met Gly Ala Ile Pro Ser Arg Trp Lys Gly
                165                 170                 175

Glu Cys Glu Ala Gly Gln Glu Phe Asn Ser Ser Met Cys Asn Ser Lys
            180                 185                 190

Leu Ile Gly Ala Arg Tyr Phe Asp Lys Gly Ile Ile Ala Ala Asn Pro
        195                 200                 205

Gly Ile Asn Ile Ser Met Lys Ser Ala Arg Asp Thr Met Gly His Gly
    210                 215                 220

Thr His Thr Ser Ser Thr Val Ala Gly Asn Tyr Val Asp Gly Val Ser
225                 230                 235                 240

Phe Phe Gly Tyr Ala Lys Gly Thr Ala Lys Gly Val Ala Pro Arg Ala
                245                 250                 255

Arg Val Ala Met Tyr Lys Val Ile Phe Asp Glu Gly Arg Tyr Ala Ser
            260                 265                 270

Asp Val Leu Ala Gly Met Asp Ala Ala Ile Ala Asp Gly Val Asp Val
        275                 280                 285

Ile Ser Ile Ser Met Gly Phe Asp Glu Thr Pro Leu Tyr Glu Asp Pro
    290                 295                 300

Ile Ala Ile Ala Ser Phe Ala Ala Thr Glu Lys Gly Val Val Val Ser
305                 310                 315                 320

Ser Ser Ala Gly Asn Ala Gly Pro Ala Leu Gly Ser Leu His Asn Gly
                325                 330                 335

Ile Pro Trp Thr Leu Thr Val Ala Ala Gly Thr Ile Asp Arg Ser Phe
            340                 345                 350

Ala Gly Thr Ile Thr Leu Gly Ser Gly Glu Thr Ile Ile Gly Trp Thr
        355                 360                 365

Met Phe Pro Ala Ser Ala Tyr Val Ala Asp Leu Pro Leu Leu Tyr Asn
    370                 375                 380

Lys Thr Tyr Ser Ala Cys Asn Ser Thr Arg Leu Leu Ser Gln Leu Arg
385                 390                 395                 400

Thr Asp Ala Ile Ile Val Cys Glu Glu Ala Glu Asp Ser Val Ser Glu
                405                 410                 415

Gln Ile Ser Val Val Ser Ala Ser Asn Ile Arg Gly Ala Ile Phe Val
```

```
                420              425              430
Ser Asp Tyr Asp Ala Glu Leu Phe Glu Leu Gly Gly Val Thr Ile Pro
            435              440              445
Gly Val Val Ile Ser Thr Lys Asp Ala Pro Ala Val Ile Ser Tyr Ala
        450              455              460
Ser Asn Asp Val Lys Pro Lys Ala Ser Ile Lys Phe Gln Gln Thr Val
465              470              475              480
Leu Gly Thr Lys Pro Ala Pro Ala Val Ala Phe Tyr Thr Ser Arg Gly
                485              490              495
Pro Ser Pro Ser Tyr Pro Gly Ile Leu Lys Pro Asp Ile Met Ala Pro
            500              505              510
Gly Ser Leu Val Phe Ala Ala Trp Ile Pro Asn Thr Ala Thr Ala Gln
        515              520              525
Ile Gly Leu Asn Thr Leu Leu Thr Ser Glu Tyr Asn Met Val Ser Gly
        530              535              540
Thr Ser Met Ala Cys Pro His Ala Ala Gly Val Ala Ala Leu Leu Lys
545              550              555              560
Gly Ala His Pro Glu Trp Ser Ala Ala Ile Arg Ser Ala Met Met
                565              570              575
Thr Thr Ala Asn Pro Leu Asp Asn Thr Leu Asn Pro Ile Arg Asp Asn
            580              585              590
Gly Leu Ile Asn Phe Thr Ser Ala Ser Pro Leu Ala Met Gly Ala Gly
        595              600              605
Gln Val Asp Pro Asn Arg Ala Leu Asp Pro Gly Leu Ile Tyr Glu Thr
        610              615              620
Thr Pro Gln Asp Tyr Val Ser Leu Leu Cys Thr Leu Asn Phe Thr Gln
625              630              635              640
Asn Gln Ile Leu Ser Ile Thr Arg Ser Asn Arg Tyr Ser Cys Ser Thr
                645              650              655
Pro Asn Pro Asp Leu Asn Tyr Pro Ser Phe Ile Thr Leu His Tyr Asn
            660              665              670
Thr Asn Ala Thr Phe Val Gln Thr Phe His Arg Thr Val Thr Asn Val
        675              680              685
Gly Gly Ser Ala Thr Thr Tyr Lys Ala Lys Ile Thr Ala Pro Leu Gly
        690              695              700
Ser Val Val Ser Val Ser Pro Asp Thr Leu Ala Phe Arg Lys Gln Tyr
705              710              715              720
Glu Gln Gln Ser Tyr Glu Leu Thr Ile Glu Tyr Lys Pro Asp Gly Glu
                725              730              735
Glu Thr Val Ser Phe Gly Glu Leu Val Trp Ile Glu Glu Asn Gly Asn
            740              745              750
His Thr Val Arg Ser Pro Ile Thr Val Ser Pro Ser Met Ser Asn Phe
        755              760              765
Val Phe Met Gly Thr Gln
    770

<210> SEQ ID NO 11
<211> LENGTH: 33
<212> TYPE: DNA
<213> ORGANISM: Artificial Sequence
<220> FEATURE:
<223> OTHER INFORMATION: Primer for 5' specific cDNA products

<400> SEQUENCE: 11
gggggatccg aggtctagga atggtgttct tca                             33
```

<210> SEQ ID NO 12
<211> LENGTH: 41
<212> TYPE: DNA
<213> ORGANISM: Artificial Sequence
<220> FEATURE:
<223> OTHER INFORMATION: Primer for 3' specific cDNA products

<400> SEQUENCE: 12
gggctcgagt tgtgtaccca taaacacaaa gttactcatg g         41

<210> SEQ ID NO 13
<211> LENGTH: 2338
<212> TYPE: DNA
<213> ORGANISM: Artificial Sequence
<220> FEATURE:
<223> OTHER INFORMATION: cDNA encoding for heterocarpine having
      undergone a deletion of the initiation codon and a deletion of the
      STOP codon

<400> SEQUENCE: 13

| | | |
|---|---|---|
| gggggatccg aggtctagga atggtgttct tcatttattc cttttcgttc ttgcatggct | 60 |
| tctgttggcg gctctccatg ctaactcaag ttcggatgag agatcaacat atatagttca | 120 |
| tatggacaag acccatatgc ccaaaaacctt ctctagcccc caccattggt actcttcgt | 180 |
| cgttcgatcc ctcaagtcta caaagccaac caaattaaat cgccgtcgat cctcaccact | 240 |
| tcttgtatac tcttacgaca atgctgctca tggtttcagt gcagttttat ctcaacagga | 300 |
| acttgaaact ctaaaaaagt ctccaggttt cgtctcagtt tatgccgata agacagcgac | 360 |
| acttgacacc acccatacac ctgaatttct ctccctgaat actgccaacg ggttgtggcc | 420 |
| tgcttcaaag tatggtgaag atataattgt tggtgttatt gacagcggtg tctggccgga | 480 |
| gagtgaaagt tataatgatg atggtatggg cgctattcca agcagatgga agggagaatg | 540 |
| tgaagctgga caagagttca attcctccat gtgcaactca aagcttattg gagctagata | 600 |
| tttcgataag ggtatcattg cggcaaatcc tgggattaac attagcatga aatctgccag | 660 |
| agatactatg gggcatggga ctcacacatc ctccacagtt gctgggaatt atgtggatgg | 720 |
| cgtttcattc tttggctatg ctaaaggtac agcaaaagga gtggcaccac gggcgagagt | 780 |
| ggctatgtac aaggtcattt ttgacgaagg gcgctatgca tctgatgttc ttgccggtat | 840 |
| ggacgcggct attgctgatg gtgttgatgt aatttcaata tcaatgggat tgatgagac | 900 |
| cccgttgtat gaagatccta tagcaattgc ctcattcgct gctacagaga agggcgtagt | 960 |
| ggtctcatct tcagcaggaa atgcagggcc agcgctaggg agcttgcaca atggaatccc | 1020 |
| atggacgtta actgttgcag ctggaaccat tgaccgttca tttgcaggca ctataactct | 1080 |
| tgggagtggg gaaaccatca ttggatggac aatgttccca gccagtgctt atgtagcaga | 1140 |
| cttgccactg ctttataaca agacttactc tgcatgcaac tcaactcgat tattatctca | 1200 |
| actccgaact gacgccatca tcgtatgcga agaagctgaa gattcggtat ctgagcaaat | 1260 |
| atctgttgtc agtgcatcga acattcgggg agccatattt gtttcagatt atgatgctga | 1320 |
| attatttgaa cttggtggtg tgactattcc tggtgtcgtg attagcacca aggatgcacc | 1380 |
| ggctgtgatc agctacgcca gcaatgatgt gaaacctaag gcaagcatca agttccaaca | 1440 |
| aactgttctg ggcacaaagc ctgcaccagc cgtggctttc tatacttcta gaggtccgtc | 1500 |
| accgagctat ccaggcatct taagccagat ataatggcc cctgggtcac tagttttttgc | 1560 |
| tgcttggatt ccaaatactg ctacagccca aattggtttg aataccctct tgacaagtga | 1620 |

-continued

```
atacaatatg gtttctggaa catcaatggc ctgccctcat gctgctggtg tagctgctct   1680
ccttaagggc gcacaccctg aatggagtgc agctgctatt aggtctgcaa tgatgactac   1740
agcaaatccc ttggataaca cactaaatcc aatccgggac aatggtctaa tcaatttcac   1800
atctgcttca cctttagcta tgggagccgg ccaagttgat cctaatcggg cacttgatcc   1860
tggtttgatt tatgaaacca ccccacaaga ttatgtgagc ctcctctgca ctctgaactt   1920
cacccaaaac caaatcctgt ccattacaag atcaaaccgt tacagctgct ccacccctaa   1980
tcctgatctt aactatcctt cttttattac tttacactac aacacaaatg caacatttgt   2040
tcagactttt cacaggactg tgactaacgt tggaggaagc gctacaactt acaaggccaa   2100
gatcactgct cctctaggtt ctgtagttag tgtctcacca gacacattgg ccttcagaaa   2160
gcagtatgag cagcagagct acgagctcac tattgagtac aagcctgatg gtgaagaaac   2220
tgtttcattt ggggaacttg tttggattga agaaaatggg aatcacactg tgaggagccc   2280
tattacagtg tcaccttcca tgagtaactt tgtgtttatg ggtacacaac tcgagccc     2338

<210> SEQ ID NO 14
<211> LENGTH: 793
<212> TYPE: PRT
<213> ORGANISM: Artificial Sequence
<220> FEATURE:
<223> OTHER INFORMATION: Recombinant heterocarpine

<400> SEQUENCE: 14

Met Ala Ile Ser Arg Glu Leu Val Asp Pro Arg Ser Arg Asn Gly Val
1               5                   10                  15

Leu His Leu Phe Leu Phe Val Leu Ala Trp Leu Leu Leu Ala Ala Leu
            20                  25                  30

His Ala Asn Ser Ser Ser Asp Glu Arg Ser Thr Tyr Ile Val His Met
        35                  40                  45

Asp Lys Thr His Met Pro Lys Thr Phe Ser Ser Pro His His Trp Tyr
    50                  55                  60

Ser Ser Val Val Arg Ser Leu Lys Ser Thr Lys Pro Thr Lys Leu Asn
65                  70                  75                  80

Arg Arg Arg Ser Ser Pro Leu Leu Val Tyr Ser Tyr Asp Asn Ala Ala
                85                  90                  95

His Gly Phe Ser Ala Val Leu Ser Gln Gln Glu Leu Glu Thr Leu Lys
            100                 105                 110

Lys Ser Pro Gly Phe Val Ser Val Tyr Ala Asp Lys Thr Ala Thr Leu
        115                 120                 125

Asp Thr Thr His Thr Pro Glu Phe Leu Ser Leu Asn Thr Ala Asn Gly
    130                 135                 140

Leu Trp Pro Ala Ser Lys Tyr Gly Glu Asp Ile Ile Val Gly Val Ile
145                 150                 155                 160

Asp Ser Gly Val Trp Pro Glu Ser Glu Ser Tyr Asn Asp Asp Gly Met
                165                 170                 175

Gly Ala Ile Pro Ser Arg Trp Lys Gly Glu Cys Glu Ala Gly Gln Glu
            180                 185                 190

Phe Asn Ser Ser Met Cys Asn Ser Lys Leu Ile Gly Ala Arg Tyr Phe
        195                 200                 205

Asp Lys Gly Ile Ile Ala Ala Asn Pro Gly Ile Asn Ile Ser Met Lys
    210                 215                 220

Ser Ala Arg Asp Thr Met Gly His Gly Thr His Thr Ser Ser Thr Val
225                 230                 235                 240
```

-continued

```
Ala Gly Asn Tyr Val Asp Gly Val Ser Phe Gly Tyr Ala Lys Gly
            245                 250                 255

Thr Ala Lys Gly Val Ala Pro Arg Ala Arg Val Ala Met Tyr Lys Val
        260                 265                 270

Ile Phe Asp Glu Gly Arg Tyr Ala Ser Asp Val Leu Ala Gly Met Asp
        275                 280                 285

Ala Ala Ile Ala Asp Gly Val Asp Val Ile Ser Ile Ser Met Gly Phe
        290                 295                 300

Asp Glu Thr Pro Leu Tyr Glu Asp Pro Ile Ala Ile Ala Ser Phe Ala
305                 310                 315                 320

Ala Thr Glu Lys Gly Val Val Ser Ser Ala Gly Asn Ala Gly
        325                 330                 335

Pro Ala Leu Gly Ser Leu His Asn Gly Ile Pro Trp Thr Leu Thr Val
        340                 345                 350

Ala Ala Gly Thr Ile Asp Arg Ser Phe Ala Gly Thr Ile Thr Leu Gly
        355                 360                 365

Ser Gly Glu Thr Ile Ile Gly Trp Thr Met Phe Pro Ala Ser Ala Tyr
    370                 375                 380

Val Ala Asp Leu Pro Leu Leu Tyr Asn Lys Thr Tyr Ser Ala Cys Asn
385                 390                 395                 400

Ser Thr Arg Leu Leu Ser Gln Leu Arg Thr Asp Ala Ile Ile Val Cys
            405                 410                 415

Glu Glu Ala Glu Asp Ser Val Ser Glu Gln Ile Ser Val Val Ser Ala
            420                 425                 430

Ser Asn Ile Arg Gly Ala Ile Phe Val Ser Asp Tyr Asp Ala Glu Leu
        435                 440                 445

Phe Glu Leu Gly Gly Val Thr Ile Pro Gly Val Val Ile Ser Thr Lys
    450                 455                 460

Asp Ala Pro Ala Val Ile Ser Tyr Ala Ser Asn Asp Val Lys Pro Lys
465                 470                 475                 480

Ala Ser Ile Lys Phe Gln Gln Thr Val Leu Gly Thr Lys Pro Ala Pro
            485                 490                 495

Ala Val Ala Phe Tyr Thr Ser Arg Gly Pro Ser Pro Ser Tyr Pro Gly
        500                 505                 510

Ile Leu Lys Pro Asp Ile Met Ala Pro Gly Ser Leu Val Phe Ala Ala
        515                 520                 525

Trp Ile Pro Asn Thr Ala Thr Ala Gln Ile Gly Leu Asn Thr Leu Leu
    530                 535                 540

Thr Ser Glu Tyr Asn Met Val Ser Gly Thr Ser Met Ala Cys Pro His
545                 550                 555                 560

Ala Ala Gly Val Ala Ala Leu Leu Lys Gly Ala His Pro Glu Trp Ser
            565                 570                 575

Ala Ala Ala Ile Arg Ser Ala Met Met Thr Thr Ala Asn Pro Leu Asp
        580                 585                 590

Asn Thr Leu Asn Pro Ile Arg Asp Asn Gly Leu Ile Asn Phe Thr Ser
        595                 600                 605

Ala Ser Pro Leu Ala Met Gly Ala Gly Gln Val Asp Pro Asn Arg Ala
        610                 615                 620

Leu Asp Pro Gly Leu Ile Tyr Glu Thr Thr Pro Gln Asp Tyr Val Ser
625                 630                 635                 640

Leu Leu Cys Thr Leu Asn Phe Thr Gln Asn Gln Ile Leu Ser Ile Thr
            645                 650                 655

Arg Ser Asn Arg Tyr Ser Cys Ser Thr Pro Asn Pro Asp Leu Asn Tyr
```

-continued

```
                660                     665                     670
Pro Ser Phe Ile Thr Leu His Tyr Asn Thr Asn Ala Thr Phe Val Gln
        675                     680                     685

Thr Phe His Arg Thr Val Thr Asn Val Gly Gly Ser Ala Thr Thr Tyr
        690                     695                     700

Lys Ala Lys Ile Thr Ala Pro Leu Gly Ser Val Val Ser Val Ser Pro
705                     710                     715                     720

Asp Thr Leu Ala Phe Arg Lys Gln Tyr Glu Gln Gln Ser Tyr Glu Leu
                725                     730                     735

Thr Ile Glu Tyr Lys Pro Asp Gly Glu Glu Thr Val Ser Phe Gly Glu
                740                     745                     750

Leu Val Trp Ile Glu Glu Asn Gly Asn His Thr Val Arg Ser Pro Ile
        755                     760                     765

Thr Val Ser Pro Ser Met Ser Asn Phe Val Phe Met Gly Thr Gln Leu
        770                     775                     780

Glu His His His His His His His
785                     790
```

The invention claimed is:

1. A process for preparing an isolated polypeptide comprising the following steps:
   (a) culturing, under suitable conditions to obtain the expression of said polypeptide, a host cell transformed or transfected with an expression vector comprising an isolated polynucleotide comprising a polynucleotide sequence of SEQ. ID. NO. 9 or SEQ ID NO. 13, and
   (b) isolating the polypeptide from the host cell cultures;
   wherein said isolated polypeptide is heterocarpine, and wherein said isolated polypeptide is associated with the modulation of cell proliferation.

2. An isolated polynucleotide comprising the nucleic acid sequence of SEQ ID NO: 4.

3. An isolated polynucleotide comprising the nucleic acid sequence of SEQ ID NO: 5.

4. An isolated polynucleotide comprising a nucleic acid sequence of SEQ ID NO: 8, wherein said polynucleotide encodes a polypeptide which is heterocarpine and wherein said polypeptide is associated with the modulation of cell proliferation.

5. An expression vector comprising the isolated polynucleotide of claim 4.

6. An isolated host cell comprising the expression vector of claim 5.

7. A method of making a polypeptide comprising culturing the host cell of claim 6 under suitable conditions to obtain expression of said polypeptide.

8. The method of claim 7, further comprising isolating said polypeptide from the host cell culture.

9. An isolated polypeptide encoded by the polynucleotide of claim 4.

10. An isolated polynucleotide comprising a nucleic acid sequence of SEQ ID NO: 9, wherein said polynucleotide encodes a polypeptide which is heterocarpine and wherein said polypeptide is associated with the modulation of cell proliferation.

11. An expression vector comprising the isolated polynucleotide of claim 10.

12. An isolated host cell comprising the expression vector of claim 11.

13. A method of making a polypeptide comprising culturing the host cell of claim 12 under suitable conditions to obtain expression of said polypeptide.

14. The method of claim 13, further comprising isolating said polypeptide from the host cell culture.

15. An isolated polypeptide encoded by the polynucleotide of claim 10.

16. An isolated polynucleotide comprising the nucleic acid sequence of SEQ ID NO: 11.

17. An isolated polynucleotide comprising the nucleic acid sequence of SEQ ID NO: 12.

18. An isolated polynucleotide comprising a nucleic acid sequence of SEQ ID NO: 13, wherein said polynucleotide encodes a polypeptide which is heterocarpine and wherein said polypeptide is associated with the modulation of cell proliferation.

19. An expression vector comprising the isolated polynucleotide of claim 18.

20. An isolated host cell comprising the expression vector of claim 19.

21. A method of making a polypeptide comprising culturing the host cell of claim 20 under suitable conditions to obtain expression of said polypeptide.

22. The method of claim 21, further comprising isolating said polypeptide from the host cell culture.

23. An isolated polypeptide encoded by the polynucleotide of claim 18.

* * * * *

UNITED STATES PATENT AND TRADEMARK OFFICE
CERTIFICATE OF CORRECTION

PATENT NO. : 7,655,438 B2  Page 1 of 1
APPLICATION NO. : 10/535545
DATED : February 2, 2010
INVENTOR(S) : Eric Ferrandis It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 944 days.

Signed and Sealed this

Twenty-third Day of November, 2010

David J. Kappos
*Director of the United States Patent and Trademark Office*